United States Patent [19]

Krause et al.

[11] Patent Number: 4,704,227
[45] Date of Patent: Nov. 3, 1987

[54] LIQUID CRYSTAL COMPOUNDS

[75] Inventors: Joachim Krause, Dieburg; Andreas Wächtler, Griesheim; Reinhard Hittich, Modautal; Georg Weber, Erzhausen; Bernhard Scheuble, Alsbach, all of Fed. Rep. of Germany

[73] Assignee: Merck Patent Gesellschaft mit beschrankter Haftung, Darmstadt, Fed. Rep. of Germany

[21] Appl. No.: 702,281

[22] Filed: Feb. 15, 1985

[30] Foreign Application Priority Data

Feb. 18, 1984 [DE] Fed. Rep. of Germany ....... 3405914

[51] Int. Cl.$^4$ ............................ C09K 3/34; G02F 1/13; C07D 319/06; C07D 339/08; C07D 409/04; C07D 405/04
[52] U.S. Cl. ............................ 252/299.61; 252/299.5; 350/350 R; 350/350 S; 549/15; 549/20; 549/21; 549/22; 549/369; 549/370; 549/371; 549/372; 549/373; 549/374; 549/375; 546/187; 546/205; 546/206; 546/207; 544/238; 544/296; 544/316; 544/318; 544/333
[58] Field of Search ............................ 252/299.61, 299.5; 350/350 R, 350 S; 549/15, 20, 21, 22, 369, 370, 371, 372, 373, 374, 375; 546/187, 205, 206, 207; 544/238, 296, 316, 318, 333

[56] References Cited

U.S. PATENT DOCUMENTS

| | | | |
|---|---|---|---|
| 4,113,647 | 9/1978 | Coates et al. | 252/299.63 |
| 4,200,580 | 4/1980 | Hsu | 252/299.61 |
| 4,237,026 | 12/1980 | Eidenshink et al. | 252/299.63 |
| 4,293,434 | 10/1981 | Deutscher et al. | 252/299.63 |
| 4,313,878 | 2/1982 | Hsu | 252/299.61 |
| 4,322,354 | 3/1982 | Sorkin | 252/299.61 |
| 4,325,830 | 4/1982 | Sethofer | 252/299.61 |
| 4,335,012 | 1/1982 | Sorkin | 252/299.61 |
| 4,344,856 | 8/1982 | Demus et al. | 252/299.61 |
| 4,348,324 | 7/1982 | Demus et al. | 252/299.61 |
| 4,357,078 | 11/1982 | Carr et al. | 252/299.63 |
| 4,368,135 | 1/1983 | Osman | 252/299.63 |
| 4,400,061 | 8/1983 | Carr et al. | 252/299.62 |
| 4,400,293 | 8/1983 | Romer et al. | 252/299.63 |
| 4,405,488 | 9/1983 | Sugimori et al. | 252/299.63 |
| 4,415,470 | 11/1983 | Eidenshink et al. | 252/299.63 |
| 4,424,371 | 1/1984 | Hsu | 252/299.61 |
| 4,478,740 | 10/1984 | Eidenschink et al. | 252/299.62 |
| 4,486,332 | 12/1984 | Demus et al. | 252/299.61 |
| 4,490,276 | 12/1984 | Hsu | 252/299.61 |
| 4,490,305 | 12/1984 | Eidenschink et al. | 252/299.63 |
| 4,505,838 | 3/1985 | Romer et al. | 252/299.5 |
| 4,510,069 | 4/1985 | Eidenschink et al. | 252/299.63 |
| 4,512,636 | 4/1985 | Andrews et al. | 252/299.61 |
| 4,521,327 | 6/1985 | Demus et al. | 252/299.61 |
| 4,536,321 | 8/1985 | Sugimori et al. | 252/299.63 |
| 4,537,698 | 8/1985 | Sucrow et al. | 252/299.61 |
| 4,542,230 | 9/1985 | Gray et al. | 252/299.65 |
| 4,548,731 | 10/1985 | Sugimori et al. | 252/299.63 |
| 4,551,264 | 11/1985 | Eidenschink et al. | 252/299.66 |
| 4,551,280 | 11/1985 | Sasaki et al. | 252/299.63 |
| 4,564,694 | 1/1986 | Hirai et al. | 252/299.65 |
| 4,565,425 | 1/1986 | Petrzilka et al. | 252/299.61 |
| 4,597,892 | 7/1986 | Zaschke et al. | 252/299.61 |
| 4,630,897 | 12/1986 | Andrews et al. | 252/299.61 |
| 4,632,515 | 12/1986 | Gray et al. | 252/299.61 |
| 4,659,502 | 4/1987 | Fearon et al. | 252/299.61 |

FOREIGN PATENT DOCUMENTS

| | | | |
|---|---|---|---|
| 19665 | 12/1980 | European Pat. Off. | 252/299.63 |
| 73378 | 3/1983 | European Pat. Off. | 252/299.63 |
| 84194 | 7/1983 | European Pat. Off. | 252/299.61 |
| 87032 | 8/1983 | European Pat. Off. | 252/299.61 |
| 87679 | 9/1983 | European Pat. Off. | 252/299.61 |
| 149238 | 7/1985 | European Pat. Off. | 252/299.61 |

(List continued on next page.)

Primary Examiner—Teddy S. Gron
Attorney, Agent, or Firm—Millen & White

[57] ABSTRACT

Compounds of the formula I

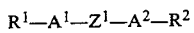

$$R^1-A^1-Z^1-A^2-R^2 \qquad I$$

wherein
R$^1$ and R$^2$ are each H, an alkyl, alkoxy, alkanoyl, alkanoyloxy or alkoxycarbonyl group with in each case 1–10 C atoms, F, Cl, Br, CN or R$^3$—A$^3$—Z$^2$—,
A$^1$ is —A—, —A$^4$—A— or —A—A$^4$—,
A is a 1,3-dioxane-2,5-diyl or a 1,3-dithiane-2,5-diyl group,
A$^2$, A$^3$ are each a 1,4-cyclohexylene, 1,3-dioxane-2,5-diyl,
and A$^4$ 1,3-dithiane-2,5-diyl, piperidine-1,4-diyl or 1,4-bicyclo(2,2,2)octylene group, or a 1,4-phenylene, pyrimidine-2,5-diyl or pyridazine-3,6-diyl group which is unsubstituted or substituted by one or two F and/or Cl atoms and/or CH$_3$ groups and/or CN groups,
Z$^1$ and Z$^2$ are each —CO—O—, —O—CO—, —CH$_2$CH$_2$—, —OCH$_2$—, —CH$_2$O— or a single bond and
R$^3$ is H, an alkyl, alkoxy, alkanoyl, alkanoyloxy or alkoxycarbonyl group with in each case 1–10 C atoms, F, Cl, Br or CN, with the proviso that
(a) at least one group A$^2$, A$^3$ and/or A$^4$ contains lateral substituents,
(b) 1,3-dioxane-2,5-diyl and 1,3-dithiane-2,5-diyl groups are not substituted by alkoxy, alkanoyl, alkanoyloxy, alkoxycarbonyl, F, Cl, Br, CN or R$^3$—A$^3$—Z$^2$ in the 2-position and piperidine-1,4-diyl groups are not substituted by these radicals in the 1-position,
(c) Z$^1$ is not —CH$_2$CH$_2$— if A$^1$ is —A— and
(d) Z$^1$ is not —CO—O— if A$^1$ is —A—A$^4$—and —A$^2$—R$^2$ is 3-chloro-4-cyanophenyl and
(e) all lateral substituents on pyrimidine-2,5-diyl and pyridazine-3,6-diyl groups are attached to C-atoms, can be used as components of liquid crystal phases.

13 Claims, No Drawings

FOREIGN PATENT DOCUMENTS

| | | | |
|---|---|---|---|
| 2243685 | 3/1973 | Fed. Rep. of Germany | 252/299.61 |
| 2939782 | 4/1981 | Fed. Rep. of Germany | 252/299.64 |
| 3315295 | 10/1984 | Fed. Rep. of Germany | 252/299.61 |
| 3328638 | 2/1985 | Fed. Rep. of Germany | 252/299.61 |
| 3404116 | 8/1985 | Fed. Rep. of Germany | 252/299.61 |
| 3407013 | 9/1985 | Fed. Rep. of Germany | 252/299.61 |
| 3410733 | 10/1985 | Fed. Rep. of Germany | 252/299.61 |
| 3411571 | 10/1985 | Fed. Rep. of Germany | 252/299.61 |
| 3410734 | 10/1985 | Fed. Rep. of Germany | 252/299.63 |
| 158480 | 1/1983 | German Democratic Rep. | 252/299.61 |
| 227719 | 9/1985 | German Democratic Rep. | 252/299.61 |
| 57-64689 | 4/1982 | Japan | 252/299.61 |
| 57-139074 | 8/1982 | Japan | 252/299.61 |
| 58-140086 | 8/1983 | Japan | 252/299.61 |
| 59-82382 | 5/1984 | Japan | 252/299.61 |
| 59-98079 | 6/1984 | Japan | 252/299.61 |
| 60-78972 | 5/1985 | Japan | 252/299.61 |
| 60-204780 | 10/1985 | Japan | 252/299.61 |
| 61-78782 | 4/1986 | Japan | 252/299.61 |
| 2092169 | 8/1982 | United Kingdom | 252/299.61 |
| 2121406 | 12/1983 | United Kingdom | 252/299.63 |
| 2134110 | 8/1984 | United Kingdom | 252/299.63 |

LIQUID CRYSTAL COMPOUNDS

BACKGROUND OF THE INVENTION

This invention relates to new compounds having valuable properties as liquid crystals.

SUMMARY OF THE INVENTION

It is an object of this invention to provide new stable liquid crystal or mesogenic compounds which are suitable as components of liquid crystal phases.

Upon further study of the specification and appended claims, further objects and advantages of this invention will become apparent to those skilled in the art.

These objects has been achieved by providing compounds of the formula I $$R^1-A^1-Z_1-A^2-R^2 \quad\quad I$$

wherein $R^1$ and $R^2$ are each H, an alkyl, alkoxy, alkanoyl, alkanoyloxy or alkoxycarbonyl group with in each case 1-10 C atoms, F, Cl, Br, CN or $R^3-A^3-Z_2-$, $A^1$ is $-A-$, $-A^4-A-$ or $-A-A^4-$, A is a 1,3-dioxane-2,5-diyl or a 1,3-dithiane-2,5-diyl group, $A^2$, $A^3$ are each a 1,4-cyclohexylene, 1,3-dioxane-2,5-diyl, and $A^4$ 1,3-dithiane-2,5-diyl, piperidine-1,4-diyl or 1,4-bicyclo(2,2,2)octylene group, or a 1,4-phenylene, pyrimidine-2,5-diyl or pyridazine-3,6-diyl group which is unsubstituted or substituted by one or two F and/or Cl atoms and/or $CH_3$ groups and/or CN groups, $Z^1$ and $Z^2$ are each $-CO-O-$, $-O-CO-$, $-CH_2CH_2-$, $-OCH_2-$, $-CH_2O-$ or a single bond and $R^3$ is H, an alkyl, alkoxy, alkanoyl, alkanoyloxy or alkoxycarbonyl group with in each case 1-10 C atoms, F, Cl, Br or CN, with the proviso that (a) at least one group $A^2$, $A^3$ and/or $A^4$ contains lateral substituents, (b) 1,3-dioxane-2,5-diyl and 1,3-dithiane-2,5-diyl groups are not substituted by alkoxy, alkanoyl, alkanoyloxy, alkoxycarbonyl, F, Cl, Br, CN or $R^3-A^3-Z^2$ in the 2-position and piperidine-1,4-diyl groups are not substituted by these radicals in the 1-position, (c) $Z^1$ is not $-CH_2CH_2-$ if $A^1$ is $-A-$ and (d) $Z^1$ is not $-CO-O-$ if $A^1$ is $-A-A^4-$ and $-A^2-R^2$ is 3-chloro-4-cyanophenyl and (e) all lateral substituents on pyrimidine-2,5-diyl and pyridazine-3,6-diyl groups are attached to C-atoms.

DETAILED DISCUSSION

For simplicity, in the following text Cy is a 1,4-cyclohexylene group, Dio is a 1,3-dioxane-2,5-diyl group, Dit is a 1,3-dithiane-2,5-diyl group, Bi is a bicyclo-(2,2,2)-octylene group, Pip is a piperidine-1,4-diyl group, Phe is a 1,4-phenylene group, Pyr is a pyrimidine-2,5-diyl group and Pyn is a pyridazine-3,6-diyl group, it being possible for Phe and/or Pyr and/or Pyn to be unsubstituted or substituted by one or two F and/or Cl atoms and/or $CH_3$ groups and/or CN groups, at least one of these groups in the compounds of the formula I containing lateral substituents.

The compounds of the formula I can be used as components of liquid crystal phases, in particular for displays which are based on the principle of the twisted cell, the guest/host effect, the effect of deformation of aligned phases or the effect of dynamic scattering.

It has been found that the compounds of the formula I are outstandingly suitable as components of liquid crystal phases. In particular, stable liquid crystal phases with a broad mesophase range and comparatively low viscosity can be prepared with the aid of these compounds.

By providing the compounds of the formula I, the range of liquid crystal substances which are suitable, from various application viewpoints, for the preparation of liquid crystal mixtures is also quite generally considerably increased.

The compounds of the formula I have a wide range of application. Depending on the choice of the substituents, these compounds can be used as base materials from which liquid crystal phases are predominantly composed; however, compounds of the formula I can also be added to liquid crystal base materials from other classes of compounds, for example in order to influence the dielectric and/or optical anisotropy of such a dielectric. The compounds of the formula I are furthermore suitable as intermediates for the preparation of other substances which can be used as constituents of liquid crystal dielectrics.

The compounds of the formula I are colorless in the pure state and form liquid crystal mesophases in a temperature range which is advantageously located for electrooptical use. They are very stable towards chemicals, heat and light.

The invention thus relates to the compounds of the formula I and to a process for the preparation of compounds of the formula I characterized in that a corresponding aldehyde is reacted with a corresponding diol or dithiol, or in that a compound which otherwise corresponds to the formula I but contains one or more reducible groups and/or C-C bonds instead of H atoms, is treated with a reducing agent, or in that, to prepare esters of the formula I (wherein $Z^1$ and/or $Z^2$ are $-CO-O-$ or $-O-CO-$ and/or $R^1$ and/or $R^2$ and/or $R^3$ contain a carboxyl group), a corresponding carboxylic acid or one of its reactive derivatives is reacted with a corresponding alcohol or one of its reactive derivatives, or in that, to prepare nitriles of the formula I (wherein $R^1$ and/or $R^2$ and/or $R^3$ are CN and/or wherein $A^2$ and/or $A^3$ and/or $A^4$ are substituted by at least one CN group), a corresponding carboxylic acid amide is dehydrated or a corresponding carboxylic acid halide is reacted with sulfamide, or in that, to prepare ethers of the formula I (wherein $R^1$ and/or $R^2$ are an alkoxy group and/or $Z^1$ and/or $Z^2$ are a $-OCH_2-$ or $-CH_2O-$ group), a corresponding hydroxy compound is etherified, and/or in that, if appropriate, a chlorine or bromine compound of the formula I (wherein $R^1$ and/or $R^2$ and/or $R^3$ are Cl or Br and/or wherein $A^2$ and/or $A^3$ and/or $A^4$ are substituted by at least one chlorine or bromine atom) is reacted with a cyanide, and/or in that, if appropriate, a base of the formula I is converted into one of its acid addition salts by treatment with an acid, or in that, if appropriate, a compound of the formula I is liberated from one of its acid addition salts by treatment with a base.

The invention furthermore relates to the use of the compounds of the formula I as components of liquid crystal phases. The invention also relates to liquid crystal phases containing at least one compound of the formula I and liquid crystal display elements containing such phases.

Above and below, $R^1$, $R^2$, $R^3$, $A^1$, $A^2$, $A^3$, $A^4$, A, $Z^1$ and $Z^2$ have the meaning given, unless expressly indicated otherwise.

If $R^1$ and $R^2$ are $R^3$—$A^3$—$Z^2$—, formula I includes compounds in which $R^3$, $A^3$ and/or $Z^2$ are identical or different.

The compounds of the formula I accordingly include compounds with two rings of the part formula Ia and Ib:

$R^1$—A—$Z^1$—$A^2$—$R^2$      Ia $R^1$—A—$A^2$—$R^2$      Ib

Compounds with three rings of the part formulae Ic to Il:

$R^1$—$A^4$—A—$Z^1$—$A^2$—$R^2$      Ic $R^1$—A—$A^4$—$Z^1$—$A^2$—$R^2$      Id $R^1$—A—$Z^1$—$A^2$—$Z^2$—$A^3$—$R^3$      Id $R^3$—$A^3$—$Z^2$—A—$Z^1$—$A^2$—$R^2$      If $R^1$—A—$Z^1$—$A^2$—$A^3$—$R^2$      Ig $R^1$—A—$A^2$—$Z^2$—$A^3$—$R^3$      Ih $R^3$—$A^3$—$Z^2$—A—$A^2$—$R^2$      Ii $R^3$—$A^3$—A—$Z^1$—$A^2$—$R^2$      Ij $R^1$—$A^4$—A—$A^2$—$R^2$      Ik $R^1$—A—$A^4$—$A^2$—$R^2$      Il,

Compounds with four rings of the part formulae Im to Iff:

$R^3$—$A^3$—$Z^2$—A—$Z^1$—$A^2$—$Z^2$—$A^3$—$R^3$      Im $R^3$—$A^3$—A—$Z^1$—$A^2$—$A^3$—$R^3$      In $R^3$—$A^3$—$Z^2$—A—$A^2$—$A^3$—$R^3$      Io $R^3$—$A^3$—A—$A^2$—$Z^2$—$A^3$—$R^3$      Ip $R^1$—$A^4$—A—$Z^1$—$A^2$—$Z^2$—$A^3$—$R^3$      Iq $R^3$—$A^3$—$Z^2$—$A^4$—A—$Z^1$—$A^2$—$R^2$      Ir $R^1$—A—$A^4$—$Z^1$—$A^2$—$Z^2$—$A^3$—$R^3$      Is $R^3$—$A^3$—$Z^2$—A—$A^4$—$Z^1$—$A^2$—$R^2$      It $R^1$—$A^4$—A—$A^2$—$A^3$—$R^3$      Iu $R^1$—A—$A^4$—$A^2$—$A^3$—$R^3$      Iv $R^1$—$A^4$—A—$A^2$—$Z^2$—$A^3$—$R^3$      Iw $R^1$—A—$A^4$—$A^2$—$Z^2$—$A^3$—$R^3$      Ix
$R^1$—$A^4$—A—$Z^1$—$A^2$—$A^3$—$R^3$      Iy $R^1$—A—$A^4$—$Z^1$—$A^2$—$A^3$—$R^3$      Iz $R^3$—$A^3$—$A^4$—A—$A^2$—$R^2$      Iaa $R^3$—$A^3$—A—$A^4$—$A^2$—$R^2$      Ibb $R^3$—$A^3$—$A^4$—A—$Z^1$—$A^2$—$R^2$      Icc $R^3$—$A^3$—A—$A^4$—$Z^1$—$A^2$—$R^2$      Idd $R^3$—$A^3$—$Z^2$—$A^4$—A—$A^2$—$R^2$      Iee $R^3$—$A^3$—$Z^2$—A—$A^4$—$A^2$—$R^2$      Iff, and compounds with five rings of the part formulae Igg to Ill:

$R^3$—$A^3$—$Z^2$—$A^4$—A—$Z^1$—$A^2$—$Z^2$—$A^3$—$R^3$      Igg $R^3$—$A^3$—$Z^2$—A—$A^4$—$Z^1$—$A^2$—$Z^2$—$A^3$—$R^3$      Ihh $R^3$—$A^3$—$A^4$—A—$A^2$—$A^3$—$R^3$      Iii $R^3$—$A^3$—A—$A^4$—$A^2$—$A^3$—$R^3$      Ijj $R^3$—$A^3$—$A^4$—A—$Z^1$—$A^2$—$A^3$—$R^3$      Ikk $R^3$—$A^3$—A—$A^4$—$Z^1$—$A^2$—$A^3$—$R^3$      Ill.

In the compounds of the formulae above and below, $R^1$ and $R^2$ are preferably alkyl, or furthermore alkoxy.

Further preferred compounds of the formulae above and below are those in which one of the radicals $R^1$ and $R^2$ is CN, F or Cl. However, such compounds preferably contain only one substituent from the series comprising Cl and N.

$A^2$, $A^3$ and $A^4$ are preferably Cy, Phe or Pyr, or furthermore preferably Dio or Dit; the compound of the formula I preferably contains not more than one of the radicals Dio, Dit, Pip, Bi, Pyn or Pyr.

Substituted unsaturated groups $A^2$, $A^3$ and/or $A^4$ include those of the structures 1 to 4,

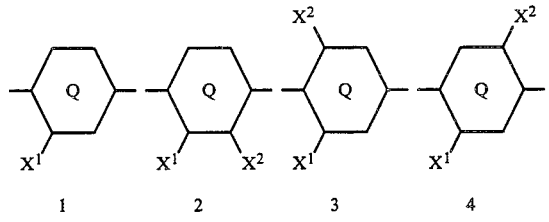

1     2     3     4 wherein the ring Q is a 1,4-phenylene group (structures 1 to 4), a pyrimidine-2,5-diyl group (structures 1 and 3) or a pyridazine-3,6-diyl group (structures 1 and 2), and $X^1$ and $X^2$ are each F and/or Cl and/or $CH_3$ and/or CN. In the case of the unsymmetric structures 1 to 4, formula I also includes their mirror images. The lateral substituents on the pyrimidinyl and pyridazinyl groups are in all cases on C-atoms.

Preferred substituted groups $A^2$, $A^3$ and/or $A^4$ are those of structures 1 and 2, in particular those of structure 1, wherein Q is preferably a 1,4-phenylene group. Preferred groups $X^1$ and/or $X^2$ are F, CN and $CH_3$, being particularly preferred. Other preferred groups are those of structure 1 wherein $X^1$ is $CH_3$.

A is preferably a 1,3-dioxane-2,5-diyl group.

$Z^1$ and $Z^2$ are preferably single bonds, and secondly preferably —CO—O— or —O—CO— groups.

$R^3$ is preferably an alkyl group with 1-10 C atoms or CN.

If $R^1$ and/or $R^2$ are alkyl radicals and/or alkoxy radicals, they can be straight-chain or branched. They are preferably straight-chain and have 2, 3, 4, 5, 6 or 7 C atoms, and accordingly are preferably ethyl, propyl, butyl, pentyl, hexyl, heptyl, ethoxy, propoxy, butoxy, pentoxy, hexoxy or heptoxy, and furthermore methyl, octyl, nonyl, decyl, methoxy, octoxy, nonoxy or decoxy.

If $R^1$ and/or $R^2$ are alkyl radicals and/or alkoxy radicals, they can be straight-chain or branced, as can be all alkyl portions of the compounds of this invention. They are preferably straight-chain and have 2, 3, 4, 5, 6, or 7 C atoms, and accordingly are preferably ethyl, propyl, butyl, pentyl, hexyl, heptyl, ethoxy, propoxy, butoxy, pentoxy, hexoxy or heptoxy, and furthermore methyl, octyl, nonyl, decyl, methoxy, octoxy, nonoxy or decoxy.

Compounds of the formulae I with branched and group substituents $R^1$ and/or $R^2$ or $R^3$ may occasionally be of importance because of a better solubility in the usual liquid crystal base materials, but especially as chiral doping substances, if they are optically active.

Branched groups of this type as a rule contain not more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

Formula I includes both the racemates of these compounds and the optical antipodes, as well as mixtures thereof.

Preferred compounds of the formulae I and Ia to Ill are those in which at least one of the radicals contained therein has one of the preferred meanings given. Particularly preferred smaller groups of compounds are those of the formulae I1 to I19:

| | |
|---|---|
| $R^1$—Dio—COO—Phe—$R^2$ | I1 |
| $R^1$—Dio—OCO—Phe—$R^2$ | I2 |
| $R^1$—Dio—Phe—OCO—Phe—$R^2$ | I3 |
| $R^1$—Dio—Phe—CH$_2$CH$_2$—Phe—$R^2$ | I4 |
| $R^1$—Dio—Phe—CH$_2$CH$_2$—Cy—$R^2$ | I5 |
| $R^1$—Dio—Phe—CH$_2$CH$_2$—Phe—Cy—$R^3$ | I6 |
| $R^1$—Dio—Phe—CH$_2$CH$_2$—Phe—Dio—$R^3$ | I7 |
| $R^1$—Dio—Phe—$R^2$ | I8 |
| $R^1$—Dio—Phe—Phe—$R^2$ | I9 |
| $R^1$—Dio—Phe—Phe—Cy—$R^3$ | I10 |
| $R^1$—Dio—Phe—Phe—Dio—$R^3$ | I11 |
| $R^1$—Dit—Phe—$R^2$ | I12 |
| $R^1$—Dio—Cy—Phe—$R^2$ | I13 |
| $R^1$—Cy—Dio—Phe—$R^2$ | I14 |
| $R^1$—Dio—Pyr—$R^2$ | I15 |
| $R^1$—Dit—Pyr—$R^2$ | I16 |
| $R^1$—Dio—CH$_2$CH$_2$—Phe—Phe—$R^2$ | I17 |
| $R^1$—Dio—CH$_2$CH$_2$—Phe—Phe—Cy—$R^2$ | I18 |
| $R^1$—Dio—CH$_2$CH$_2$—Phe—Cy—$R^2$ | I19 |

Compounds of the formula I20

| | |
|---|---|
| $R^1$—Dio—$A^4$—CO—O—Q—CN | I20 | wherein Q is 3-fluoro-1,4-phenylene and $A^4$ is Phe or Cy, are furthermore preferred.

In the compounds of the formula I, those stereoisomers in which the rings Cy, Dio, Dit and/or Pip are trans-1,4-disubstituted are preferred. Those of the abovementioned formulae which contain one or more groups Dio, Dit, Pip and/or Pyr in each case include the two possible 2,5-(Dio, Dit, Pyr) or 1,4-(Pip) position isomers.

Compounds of the formula I wherein $R^1$ and $R^2$ are each straight-chain or at most singly branched alkyl groups or alkoxy groups with 1–10 C atoms, F, Cl, Br or CN are particularly preferred.

The compounds of the formula I are prepared by methods which are known per se, such as are described in the literature (for example in the standard works, such as Houben-Weyl, Methoden der Organischen Chemie [Methods of organic chemistry], Georg-Thieme-Verlage, Stuttgart), and in particular under reaction conditions which are known and suitable for the reactions mentioned. It is also possible to utilize variants which are known per se but are not mentioned in more detail here.

If desired, the starting substances can also be formed in situ, so that they are not isolated from the reaction mixture but are immediately reacted further to give the compounds of the formula I.

The compounds of the formula I can thus be prepared by reacting a corresponding aldehyde or one of its reactive derivatives with a corresponding diol or dithiol.

The expert can find corresponding synthesis methods from the prior art by routine methods (for example German Offenlegungsschrift No. 2,944,905; German Offenlegungsschrift No. 3,227,916; East German Patent Specification No. 160,061; U.S. Pat. No. 4,322,354; U.S. Pat. No. 4,298,528; U.S. Pat. No. 4,323,504; U.S. Pat. No. 4,200,580 and U.S. Pat. No. 4,313,878).

The reactants or their reactive derivatives are advantageously reacted with one another in the presence of an inert solvent, such as benzene or toluene, and/or a catalyst, for example a strong acid, such as sulfuric acid or benzene- or p-toluenesulfonic acid, or a Lewis acid, such as aluminum choride, at temperatures between about 20° and about 150° C., preferably between 80° and 120° C.

Suitable reactive derivatives of the starting substances are, above all, acetals.

The aldehydes and 1,3-diols or 1,3-dithiols mentioned and their reactive derivatives are known in some cases, and some of them can be prepared without difficulty by standard methods of organic chemistry from compounds which are known from the literature. For example the aldehydes can be obtained by oxidation of corresponding alcohols or by reduction of corresponding carboxylic acids or their derivatives, the diols can be obtained by reduction of corresponding diesters and the dithiols can be obtained by reaction of corresponding dihalides with NaSH.

Compounds of the formula I can furthermore be obtained by reducing a compound which otherwise corresponds to the formula I but contains one or more reducible groups and/or C—C bonds instead of H atoms.

Preferred possible reducible groups are carbonyl groups, in particular keto groups, and furthermore, for example, free or esterified hydroxyl groups or aromatically bonded halogen atoms. Preferred starting substances for the reduction correspond to the formula I, but can contain a cyclohexene ring or cyclohexanone ring instead of a cyclohexane ring and/or a —CH=CH— group instead of a —CH$_2$CH$_2$— group, and/or a —CO— group instead of a —CH$_2$— group, and/or a free or functionally modified OH group (for example in the form of its p-toluenesulfonate) instead of an H atom.

The reduction can be carried out, for example, by catalytic hydrogenation at temperatures between about 0° and about 200° C. and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Catalysts which are advantageously suitable are noble metals, such as Pt or Pd, which can be used in the form of oxides (for example PtO$_2$ or PdO), on a support (for example Pd-on-charcoal, -calcium carbonate or -strontium carbonate) or in finely divided form.

Ketones can also be reduced by the methods of Clemmensen (with zinc, zinc amalgam or tin and hydrochloric acid, advantageously in aqueous-alcoholic solution or in a heterogeneous phase system with water/toluene at temperatures between about 80° and 120° C.) or WolffKishner (with hydrazine, advantageously in the presence of alkali, such as KOH or NaOH, in a high-boiling solvent, such as diethylene glycol or triethylene glycol, at temperatures between about 100° and 200° C.) to give the corresponding compounds of the formula I containing alkyl groups and/or —CH$_2$CH$_2$— bridges.

Reductions with complex hydrides are also possible. For example, arylsulfonyloxy groups can be removed by reduction with LiAlH$_4$, and in particular p-toluenesulfonyloxymethyl groups can be reduced to methyl groups, advantageously in an inert solvent, such as diethyl ether or THF, at temperatures between about 0° and 100°. Double bonds can (even in the presence of CN groups!) be hydrogenated with NaBH$_4$ or tributyl-tin-hydride in methanol.

Esters of the formual I can also be obtained by esterification of corresponding carboxylic acids (or their reactive derivatives) with alcohols or phenols (or their reactive derivatives).

Particularly suitable reactive derivatives of the carboxylic acids mentioned are the acid halides, in particular the chlorides and bromides, and furthermore the anhydrides, for example also mixed anhydrides, azides or esters, in particular alkyl esters with 1-4 C atoms in the alkyl group.

Possible reactive derivatives of the alcohols or phenols mentioned are, in particular, the corresponding metal alcoholates or phenolates, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as dimethylformamide or phosphoric acid hexamethyltriamide, hydrocarbons, such as benzene, toluene or xylene, halogenohydrocarbons, such as carbon tetrachloride or tetrachloroethylene, and sulfoxides, such as dimethyl sulfoxide or sulfolane. Water-immiscible solvents can advantageously be used at the same time for azeotropic removal by distillation of the water formed during the esterification. An excess of an organic base, for example pyridine, quinoline or triethylamine, may occasionally also be used as the solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions have as a rule ended after 15 minutes to 48 hours.

In detail, the reaction conditions for the esterification largely depend on the nature of the starting substances used. Thus, a free carboxylic acid is reacted with a free alcohol or phenol as a rule in the presence of a strong acid, for example a mineral acid, such as hydrochloric acid or sulfuric acid. A preferred mode of reaction is the reaction of an acid anhydride or, in particular, an acid chloride with an alcohol, preferably in a basic medium, bases which are of significance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. Another preferred embodiment of the esterification comprises first converting the alcohol or phenol into the sodium or potassium alcoholate or phenolate, for example by treatment with ethanolic sodium hydroxide solution or potassium hydroxide solution, isolating this product and suspending it in acetone or diethyl ether together with sodium bicarbonate or potassium carbonate, with stirring, and adding a solution of the acid chloride or anhydride in diethyl ether, acetone or dimethylformamide to this suspension, advantageously at temperatures between about −25° and +20°.

To prepare nitriles of the formula I (wherein $R^1$ and/or $R^2$ are CN and/or wherein $A^2$, $A^3$ and/or $A^4$ are substituted by at least one CN group), corresponding acid amides, for example those in which the radical X is replaced by a CONH$_2$ group, can be dehydrated. The amides can be obtained, for example, from corresponding esters or acid halides by reaction with ammonia. Examples of suitable dehydrating agents are inorganic acid chlorides, such as SOCl$_2$, PCl$_3$, PCl$_5$, POCl$_3$, SO$_2$Cl$_2$, or COCl$_2$, and furthermore P$_2$O$_5$, P$_2$S$_5$, AlCl$_3$ (for example as a double compound with NaCl) and aromatic sulfonic acids and sulfonic acid halides. The reaction can be carried out in the presence or absence of an inert solvent at temperatures between about 0° and 150°; examples of possible solvents are bases, such as pyridine or triethylamine, aromatic hydrocarbons, such as benzene, toluene or xylene, or amides, such as dimethylformamide.

To prepare the abovementioned nitriles of the formula I, it is also possible to react corresponding acid halides, preferably the chlorides, with sulfamide, advantageously in an inert solvent, such as tetramethylene sulfone, at temperatures between about 80° and 150°, preferably at 120°. After customary working-up, the nitriles can be isolated directly.

Ethers of the formula I (wherein $R^1$ and/or $R^2$ and/or $R^3$ are the alkoxy group and/or wherein $Z^1$ and/or $Z^2$ are a —OCH$_2$— or —CH$_2$O— group) can be obtained by etherification of corresponding hydroxy compounds, preferably corresponding phenols, the hydroxy compound advantageously first being converted into a corresponding metal derivative, for example into the corresponding alkali metal alcoholate or alkali metal phenolate by treatment with NaH, NaNH$_2$, NaOH, KOH, Na$_2$CO$_3$ or K$_2$CO$_3$. This product can then be reacted with the corresponding alkyl halide or sulfonate or dialkyl sulfate, advantageously in an inert solvent, such as acetone, 1,2-dimethoxyethane, dimethylformamide or dimethylsulfoxide, or an excess of aqueous or aqueous-alcoholic NaOH or KOH, at temperatures between about 20° and 100°.

To prepare nitriles of the formula I (wherein $R^1$ and/or $R^2$ are CN and/or wherein $A^2$, $A^3$ and/or $A^4$ are substituted by at least one CN group), it is also possible to react corresponding chlorine or bromine compounds of the formula I (wherein $R^1$ and/or $R^2$ are Cl or Br and/or wherein A is substituted by at least one Cl or Br atom) with a cyanide, advantageously with a metal cyanide, such as NaCN, KCN or Cu$_2$(CN)$_2$, for example in the presence of pyridine in an inert solvent, such as dimethylformamide or N-methylpyrrolidone, at temperatures between 20° and 200°.

A base of the formula I can be converted with an acid into the associated acid addition salt. For this reaction, it is possible to use inorganic acids, for example sulfuric acid, nitric acid, hydrogen halide acids, such as hydrochloric acid or hydrobromic acid, phosphoric acids, such as orthophosphoric acid, or sulfamic acid, and furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-mono- and di-sulfonic acids and lauryl-sulfuric acid.

Conversely, it is possible to liberate from an acid addition salt of a compound of the formula I the base of the compound of the formula I by treatment with a base, for example with a strong inorganic base, such as KOH or NaOH.

The liquid crystal phases according to the invention comprise 2 to 20, preferably 3 to 15, components, at least one of which is a compound of the formula I. The other constituents are preferably selected from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4′-bis-cyclohexylbiphenyls, phenyl- or cyclohexyl-pyrimidines, phenyl- or cyclohexyl-dioxanes, phenyl- or cyclohexyl-dithianes, 1,2-bis-phenylethanes, 1,2-bis-cyclohexylethanes, 1-phenyl-2-cyclohexylethanes, optionally halogenated stilbenes, benzylphenyl ethers, tolanes and substituted cinnamic acids.

The most important compounds which are suitable as constituents of such liquid crystal phases can be characterised by the formula II

R′—L—G—E—R″           II wherein L and E are each a carbocyclic or heterocyclic ring system from the group formed by 1,4-disubstituted benzene and cyclohexane rings, 4,4′-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| | |
|---|---|
| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond, Y is halogen, preferably chlorine, or —CN, and R′ and R″ are alkyl, alkoxy, alkanoyloxy or alkoxycarbonyloxy with up to 18, preferably up to 8, carbon atoms, or one of these radicals is also CN, NC, NO$_2$, CF$_3$, F, Cl or Br.

In most of these compounds, R′ and R″ differ from each other, one of these radicals usually being an alkyl or alkoxy group. However, other variants of the substituents envisaged are also customary. Many such substances or mixtures thereof are commercially available. All of these substances can be prepared by methods which are known from the literature.

The liquid crystal phases according to the invention contain about 0.1 to 99%, preferably 10 to 95%, of one or more compounds of the formula I. Liquid crystal phases containing 0.1-50%, in particular 0.5-30%, of one or more compounds of the formula I are furthermore preferred.

The liquid crystal phases according to the invention are prepared in a manner which is customary per se. As a rule, the components are dissolved in one another, advantageously at elevated temperature.

The liquid crystal phases according to the invention can be modified by suitable additives so that they can be used in all the types of liquid crystal display elements which have hitherto been disclosed.

Such additives are known to the expert and are described in detail in the literature. For example, it is possible to add conductive salts, preferably ethyldimethyl-dodecyl-ammonium 4-hexyloxybenzoate, tetrabutylammonium tetraphenylboranate or complex salts of crown ethers (compare, for example, I. Haller et al., Mol. Cryst. Liq. Cryst. volume 24, pages 249–258 (1973)) to improve the conductivity, dichroic dyestuffs to prepare colored guest/host systems, or substances for modifying the dielectric anisotropy, the viscosity and/or the alignment of the nematic phases. Such substances are described, for example, in German Offenlegungsschriften 2,209,127, 2,240,864, 2,321,632, 2,338,281, 2,450,088, 2,637,430, 2,853,728 and 2,902,177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. is the melting point and c.p. is the clear point of a liquid crystal substance.

"Customary working up" means: water is added, the mixture is extracted with methylene chloride, the organic phase is separated off, dried and evaporated and the product is purified by crystallization and/or chromatography.

EXAMPLE 1

6.2 g of terephthalaldehydic acid 2-cyano-4-butylphenyl ester (obtainable by reacting terephthalaldehydic acid chloride with 3-cyano-4-n-butylphenol in the presence of pyridine) and 3.3 g of 2-pentylpropane-1,3-diol are dissolved in toluene, a spatula tip of p-toluenesulfonic acid is added and the mixture is heated, using a water separator, until no further water is formed. After cooling, the reaction mixture is washed with bicarbonate solution until free from acid, dried over sodium sulfate and worked up in the customary manner. 3-Cyano-4-butylphenyl 4-(5-pentyl-1,3-dioxan-2-yl)-benzoate of m.p. 47° and c.p. 121° is obtained.

The following compounds are prepared analogously:

3-cyano-4-ethylphenyl 4-(5-pentyl-1,3-dioxan-2-yl)-benzoate
3-cyano-4-propylphenyl 4-(5-pentyl-1,3-dioxan-2-yl)-benzoate
3-cyano-4-pentylphenyl 4-(5-pentyl-1,3-dioxan-2-yl)-benzoate
3-cyano-4-heptylphenyl 4-(5-pentyl-1,3-dioxan-2-yl)-benzoate
3-cyano-4-ethoxyphenyl 4-(5-pentyl-1,3-dioxan-2-yl)-benzoate
3-cyano-4-propoxyphenyl 4-(5-pentyl-1,3-dioxan-2-yl)-benzoate
3-cyano-4-butoxyphenyl 4-(5-pentyl-1,3-dioxan-2-yl)-benzoate
3-cyano-4-pentoxyphenyl 4-(5-pentyl-1,3-dioxan-2-yl)-benzoate
3-cyano-4-hexoxyphenyl 4-(5-pentyl-1,3-dioxan-2-yl)-benzoate
3-cyano-4-heptoxyphenyl 4-(5-pentyl-1,3-dioxan-2-yl)-benzoate
2-fluoro-4-ethylphenyl 4-(5-pentyl-1,3-dioxan-2-yl)-benzoate
2-fluoro-4-propylphenyl 4-(5-pentyl-1,3-dioxan-2-yl)-benzoate
2-fluoro-4-pentylphenyl 4-(5-pentyl-1,3-dioxan-2-yl)-benzoate
2-fluoro-4-heptylphenyl 4-(5-pentyl-1,3-dioxan-2-yl)-benzoate
2-fluoro-4-ethoxyphenyl 4-(5-pentyl-1,3-dioxan-2-yl)-benzoate
2-fluoro-4-propoxyphenyl 4-(5-pentyl-1,3-dioxan-2-yl)-benzoate
2-fluoro-4-butoxyphenyl 4-(5-pentyl-1,3-dioxan-2-yl)-benzoate
2-fluoro-4-pentoxyphenyl 4-(5-pentyl-1,3-dioxan-2-yl)-benzoate
2-fluoro-4-hexoxyphenyl 4-(5-pentyl-1,3-dioxan-2-yl)-benzoate
2-fluoro-4-heptoxyphenyl 4-(5-pentyl-1,3-dioxan-2-yl)-benzoate
2-methyl-4-ethylphenyl 4-(5-pentyl-1,3-dioxan-2-yl)-benzoate
2-methyl-4-propylphenyl 4-(5-pentyl-1,3-dioxan-2-yl)-benzoate
2-methyl-4-pentylphenyl 4-(5-pentyl-1,3-dioxan-2-yl)-benzoate
2-methyl-4-heptylphenyl 4-(5-pentyl-1,3-dioxan-2-yl)-benzoate
2-methyl-4-ethoxyphenyl 4-(5-pentyl-1,3-dioxan-2-yl)-benzoate
2-methyl-4-propoxyphenyl 4-(5-pentyl-1,3-dioxan-2-yl)-benzoate
2-methyl-4-butoxyphenyl 4-(5-pentyl-1,3-dioxan-2-yl)-benzoate
2-methyl-4-pentoxyphenyl 4-(5-pentyl-1,3-dioxan-2-yl)-benzoate
2-methyl-4-hexoxyphenyl 4-(5-pentyl-1,3-dioxan-2-yl)-benzoate
2-methyl-4-heptoxyphenyl 4-(5-pentyl-1,3-dioxan-2-yl)-benzoate
2-cyano-4-ethylphenyl 4-(5-pentyl-1,3-dioxan-2-yl)-cyclohexanecarboxylate
2-cyano-4-propylphenyl 4-(5-pentyl-1,3-dioxan-2-yl)-cyclohexanecarboxylate
2-cyano-4-pentylphenyl 4-(5-pentyl-1,3-dioxan-2-yl)-cyclohexanecarboxylate
2-cyano-4-heptylphenyl 4-(5-pentyl-1,3-dioxan-2-yl)-cyclohexanecarboxylate
2-cyano-4-ethoxyphenyl 4-(5-pentyl-1,3-dioxan-2-yl)-cyclohexanecarboxylate
2-cyano-4-propoxyphenyl 4-(5-pentyl-1,3-dioxan-2-yl)-cyclohexanecarboxylate
2-cyano-4-butoxyphenyl 4-(5-pentyl-1,3-dioxan-2-yl)-cyclohexanecarboxylate
2-cyano-4-pentoxyphenyl 4-(5-pentyl-1,3-dioxan-2-yl)-cyclohexanecarboxylate
2-cyano-4-hexoxyphenyl 4-(5-pentyl-1,3-dioxan-2-yl)-cyclohexanecarboxylate
2-cyano-4-heptoxyphenyl 4-(5-pentyl-1,3-dioxan-2-yl)-cyclohexanecarboxylate
2-fluoro-4-ethylphenyl 4-(5-pentyl-1,3-dioxan-2-yl)-cyclohexanecarboxylate
2-fluoro-4-ethylpropyl 4-(5-pentyl-1,3-dioxan-2-yl)-cyclohexanecarboxylate
2-fluoro-4-pentylphenyl 4-(5-pentyl-1,3-dioxan-2-yl)-cyclohexanecarboxylate
2-fluoro-4-heptylphenyl 4-(5-pentyl-1,3-dioxan-2-yl)-cyclohexanecarboxylate 2-fluoro-4-ethoxyphenyl 4-(5-pentyl-1,3-dioxan-2-yl)-cyclohexanecarboxylate
2-fluoro-4-propoxyphenyl 4-(5-pentyl-1,3-dioxan-2-yl)-cyclohexanecarboxylate
2-fluoro-4-butoxyphenyl 4-(5-pentyl-1,3-dioxan-2-yl)-cyclohexanecarboxylate
2-fluoro-4-pentoxyphenyl 4-(5-pentyl-1,3-dioxan-2-yl)-cyclohexanecarboxylate
2-fluoro-4-hexoxyphenyl 4-(5-pentyl-1,3-dioxan-2-yl)-cyclohexanecarboxylate
2-fluoro-4-heptoxyphenyl 4-(5-pentyl-1,3-dioxan-2-yl)-cyclohexanecarboxylate
2-methyl-4-ethylphenyl 4-(5-pentyl-1,3-dioxan-2-yl)-cyclohexanecarboxylate
2-methyl-4-propylphenyl 4-(5-pentyl-1,3-dioxan-2-yl)-cyclohexanecarboxylate
2-methyl-4-pentylphenyl 4-(5-pentyl-1,3-dioxan-2-yl)-cyclohexanecarboxylate
2-methyl-4-heptylphenyl 4-(5-pentyl-1,3-dioxan-2-yl)-cyclohexanecarboxylate
2-methyl-4-ethoxyphenyl 4-(5-pentyl-1,3-dioxan-2-yl)-cyclohexanecarboxylate
2-methyl-4-propoxyphenyl 4-(5-pentyl-1,3-dioxan-2-yl)-cyclohexanecarboxylate
2-methyl-4-butoxyphenyl 4-(5-pentyl-1,3-dioxan-2-yl)-cyclohexanecarboxylate
2-methyl-4-pentoxyphenyl 4-(5-pentyl-1,3-dioxan-2-yl)-cyclohexanecarboxylate
2-methyl-4-hexoxyphenyl 4-(5-pentyl-1,3-dioxan-2-yl)-cyclohexanecarboxylate
2-methyl-4-heptoxyphenyl 4-(5-pentyl-1,3-dioxan-2-yl)-cyclohexanecarboxylate The following compounds are prepared analogously by esterification of the appropriate carboxylic acid with 3-fluor-4-cyano-phenol:
3-fluoro-4-cyanophenyl 4-(5-ethyl-1,3-dioxan-2-yl)-benzoate
3-fluoro-4-cyanophenyl 4-(5-propyl-1,3-dioxan-2-yl)-benzoate
3-fluoro-4-cyanophenyl 4-(5-butyl-1,3-dioxan-2-yl)-benzoate
3-fluoro-4-cyanophenyl 4-(5-pentyl-1,3-dioxan-2-yl)-benzoate
3-fluoro-4-cyanophenyl 4-(5-hexyl-1,3-dioxan-2-yl)-benzoate
3-fluoro-4-cyanophenyl 4-(5-heptyl-1,3-dioxan-2-yl)-benzoate
3-fluoro-4-cyanophenyl 4-(5-octyl-1,3-dioxan-2-yl)-benzoate
3-fluoro-4-cyanophenyl 4-(5-nonyl-1,3-dioxan-2-yl)-benzoate
3-fluoro-4-cyanophenyl 4-(5-decyl-1,3-dioxan-2-yl)-benzoate
3-fluoro-4-cyanophenyl 4-(5-ethyl-1,3-dioxan-2-yl)-cyclohexancarboxylate
3-fluoro-4-cyanophenyl 4-(5-propyl-1,3-dioxan-2-yl)-cyclohexancarboxylate
3-fluoro-4-cyanophenyl 4-(5-butyl-1,3-dioxan-2-yl)-cyclohexancarboxylate
3-fluoro-4-cyanophenyl 4-(5-pentyl-1,3-dioxan-2-yl)-cyclohexancarboxylate
3-fluoro-4-cyanophenyl 4-(5-hexyl-1,3-dioxan-2-yl)-cyclohexancarboxylate
3-fluoro-4-cyanophenyl 4-(5-heptyl-1,3-dioxan-2-yl)-cyclohexancarboxylate
3-fluoro-4-cyanophenyl 4-(5-octyl-1,3-dioxan-2-yl)-cyclohexancarboxylate
3-fluoro-4-cyanophenyl 4-(5-nonyl-1,3-dioxan-2-yl)-cyclohexancarboxylate
3-fluoro-4-cyanophenyl 4-(5-decyl-1,3-dioxan-2-yl)-cyclohexancarboxylate

EXAMPLE 2

6.5 g of 4-(trans-4-propylcyclohexyl)-2-fluorobiphenyl-4'-carbaldehyde (obtainable by bromination of 4-(trans-4-propylcyclohexyl)-2-fluorobiphenyl with bromine in the presence of catalytic amounts of iodine and reaction of the oganomagnesium compound obtained from the bromine compound with N-formylpiperidine) and 3.5 g of 2-heptylpropane-1,3-diol are heated together with 1 g of strongly acid cation exchanger in 100 ml of toluene for 8 hours, using a water separator. The catalyst is then filtered off and the toluene is distilled off. After customary working-up, 4-(trans-4-propylcyclohexyl)-2-fluoro-4'-(5-heptyl-1,3-dioxan-2-yl)-biphenyl is obtained.

The following compounds are prepared analogously:
4-(trans-4-ethyl-cyclohexyl)-2-fluoro-4'-(5-heptyl-1,3-dioxan-2-yl)-biphenyl
4-(trans-4-butyl-cyclohexyl)-2-fluoro-4'-(5-heptyl-1,3-dioxan-2-yl)-biphenyl
4-(trans-4-pentyl-cyclohexyl)-2-fluoro-4'-(5-heptyl-1,3-dioxan-2-yl)-biphenyl
4-(trans-4-heptyl-cyclohexyl)-2-fluoro-4'-(5-heptyl-1,3-dioxan-2-yl)-biphenyl
4-(trans-4-ethylcyclohexyl)-2-fluoro-4'-(5-pentyl-1,3-dioxan-2-yl)-biphenyl
4-(trans-4-propylcyclohexyl)-2-fluoro-4'-(5-pentyl-1,3-dioxan-2-yl)-biphenyl
4-(trans-4-butylcyclohexyl)-2-fluoro-4'-(5-pentyl-1,3-dioxan-2-yl)-biphenyl
4-(trans-4-pentylcyclohexyl)-2-fluoro-4'-(5-pentyl-1,3-dioxan-2-yl)-biphenyl
4-(trans-4-heptylcyclohexyl)-2-fluoro-4'-(5-pentyl-1,3-dioxan-2-yl)-biphenyl
4-(trans-4-ethylcyclohexyl)-2'-fluoro-4'-(5-pentyl-1,3-dioxan-2-yl)-biphenyl
4-(trans-4-propylcyclohexyl)-2'-fluoro-4'-(5-pentyl-1,3-dioxan-2-yl)-biphenyl
4-(trans-4-butylcyclohexyl)-2'-fluoro-4'-(5-pentyl-1,3-dioxan-2-yl)-biphenyl
4-(trans-4-pentylcyclohexyl)-2'-fluoro-4'-(5-pentyl-1,3-dioxan-2-yl)-biphenyl
4-(trans-4-heptylcyclohexyl)-2'-fluoro-4'-(5-pentyl-1,3-dioxan-2-yl)-biphenyl
4-(trans-4-ethylcyclohexyl)-2-methyl-4'-(5-pentyl-1,3-dioxan-2-yl)-biphenyl
4-(trans-4-propylcyclohexyl)-2-methyl-4'-(5-pentyl-1,3-dioxan-2-yl)-biphenyl
4-(trans-4-butylcyclohexyl)-2-methyl-4'-(5-pentyl-1,3-dioxan-2-yl)-biphenyl
4-(trans-4-pentylcyclohexyl)-2-methyl-4'-(5-pentyl-1,3-dioxan-2-yl)-biphenyl
4-(trans-4-heptylcyclohexyl)-2-methyl-4'-(5-pentyl-1,3-dioxan-2-yl)-biphenyl
4-(trans-4-ethylcyclohexyl)-2-methyl-4'-(5-pentyl-1,3-dioxan-2-yl)-biphenyl
4-(trans-4-propylcyclohexyl)-2-methyl-4'-(5-pentyl-1,3-dioxan-2-yl)-biphenyl
4-(trans-4-butylcyclohexyl)-2-methyl-4'-(5-pentyl-1,3-dioxan-2-yl)-biphenyl
4-(trans-4-pentylcyclohexyl)-2-methyl-4'-(5-pentyl-1,3-dioxan-2-yl)-biphenyl, m.p. 79°, c.p. 269°
4-(trans-4-heptylcyclohexyl)-2-methyl-4'-(5-pentyl-1,3-dioxan-2-yl)-biphenyl 4-(trans-4-ethylcyclohexyl)-2-fluoro-4'-(5-hentyl-1,3-dithian-2-yl)-biphenyl
4-(trans-4-propylcyclohexyl)-2-fluoro-4'-(5-pentyl-1,3-dithian-2-yl)-biphenyl
4-(trans-4-butylcyclohexyl)-2-fluoro-4'-(5-pentyl-1,3-dithian-2-yl)-biphenyl
4-(trans-4-pentylcyclohexyl)-2-fluoro-4'-(5-pentyl-1,3-dithian-2-yl)-biphenyl
4-(trans-4-heptylcyclohexyl)-2-fluoro-4'-(5-pentyl-1,3-dithian-2-yl)-biphenyl
4-(5-ethyl-1,3-dioxan-2-yl)-2-fluoro-4'-(5-pentyl-1,3-dioxan-2-yl)-biphenyl
4-(5-propyl-1,3-dioxan-2-yl)-2-fluoro-4'-(5-pentyl-1,3-dioxan-2-yl)-biphenyl
4-(5-butyl-1,3-dioxan-2-yl)-2-fluoro-4'-(5-pentyl-1,3-dioxan-2-yl)-biphenyl
4-(5-hexyl-1,3-dioxan-2-yl)-2-fluoro-4'-(5-pentyl-1,3-dioxan-2-yl)-biphenyl
4-(5-heptyl-1,3-dioxan-2-yl)-2-fluoro-4'-(5-pentyl-1,3-dioxan-2-yl)-biphenyl
4-(trans-4-ethylcyclohexyl)-2-fluoro-4'-(5-propyl-1,3-dioxan-2-yl)-biphenyl
4-(trans-4-propylcyclohexyl)-2-fluoro-4'-(5-propyl-1,3-dioxan-2-yl)-biphenyl
4-(trans-4-butylcyclohexyl)-2-fluoro-4'-(5-propyl-1,3-dioxan-2-yl)-biphenyl
4-(trans-4-pentylcyclohexyl)-2-fluoro-4'-(5-propyl-1,3-dioxan-2-yl)-biphenyl, m.p. 83°, c.p. 272°
4-(trans-4-heptylcyclohexyl)-2-fluoro-4'-(5-propyl-1,3-dioxan-2-yl)-biphenyl
4-(5-pentyl-1,3-dioxan-2-yl)-2-cyano-1-ethyl-benzene
4-(5-pentyl-1,3-dioxan-2-yl)-2-cyano-1-propyl-benzene
4-(5-pentyl-1,3-dioxan-2-yl)-2-cyano-1-butyl-benzene
4-(5-pentyl-1,3-dioxan-2-yl)-2-cyano-1-pentyl-benzene
4-(5-pentyl-1,3-dioxan-2-yl)-2-cyano-1-heptyl-benzene
4-(5-propyl-1,3-dioxan-2-yl)-2-fluoro-1-ethyl-benzene
4-(5-propyl-1,3-dioxan-2-yl)-2-fluoro-1-propyl-benzene
4-(5-propyl-1,3-dioxan-2-yl)-2-fluoro-1-butyl-benzene
4-(5-propyl-1,3-dioxan-2-yl)-2-fluoro-1-pentyl-benzene
4-(5-propyl-1,3-dioxan-2-yl)-2-fluoro-1-heptyl-benzene
4-(5-propyl-1,3-dithian-2-yl)-2-fluoro-1-ethyl-benzene
4-(5-propyl-1,3-dithian-1-yl)-2-fluoro-1-propyl-benzene
4-(5-propyl-1,3-dithian-2-yl)-2-fluoro-1-butyl-benzene
4-(5-propyl-1,3-dithian-2-yl)-2-fluoro-1-pentyl-benzene
4-(5-propyl-1,3-dithian-2-yl)-2-fluoro-1-heptyl-benzene
4-(5-pentyl-1,3-dithian-2-yl)-2-cyano-1-ethyl-benzene
4-(5-pentyl-1,3-dithian-2-yl)-2-cyano-1-propyl-benzene
4-(5-pentyl-1,3-dithian-2-yl)-2-cyano-1-butyl-benzene
4-(5-pentyl-1,3-dithian-2-yl)-2-cyano-1-pentyl-benzene
4-(5-pentyl-1,3-dithian-2-yl)-2-cyano-1-heptyl-benzene
4-(5-pentyl-1,3-dioxan-2-yl)-2-fluoro-4'-ethyl-biphenyl
4-(5-pentyl-1,3-dioxan-2-yl)-2-fluoro-4'-propyl-biphenyl
4-(5-pentyl-1,3-dioxan-2-yl)-2-fluoro-4'-butyl-biphenyl
4-(5-pentyl-1,3-dioxan-2-yl)-2-fluoro-4'-pentyl-biphenyl
4-(5-pentyl-1,3-dioxan-2-yl)-2-fluoro-4'-heptyl-biphenyl
4-(5-heptyl-1,3-dioxan-2-yl)-2'-fluoro-4'-ethyl-biphenyl
4-(5-heptyl-1,3-dioxan-2-yl)-2'-fluoro-4'-propyl-biphenyl
4-(5-heptyl-1,3-dioxan-2-yl)-2'-fluoro-4'-butyl-biphenyl
4-(5-heptyl-1,3-dioxan-2-yl)-2'-fluoro-4'-pentyl-biphenyl
4-(5-heptyl-1,3-dioxan-2-yl)-2'-fluoro-4'-heptyl-biphenyl
4-(5-ethyl-1,3-dioxan-2-yl)-2-methyl-4'-ethyl-biphenyl
4-(5-ethyl-1,3-dioxan-2-yl)-2-methyl-4'-propyl-biphenyl
4-(5-ethyl-1,3-dioxan-2-yl)-2-methyl-4'-butyl-biphenyl
4-(5-ethyl-1,3-dioxan-2-yl)-2-methyl-4'-pentyl-biphenyl
4-(5-ethyl-1,3-dioxan-2-yl)-2-methyl-4'-heptyl-biphenyl
4-(5-butyl-1,3-dithian-2-yl)-2'-fluoro-4'-ethyl-biphenyl
4-(5-butyl-1,3-dithian-2-yl)-2'-fluoro-4'-propyl-biphenyl
4-(5-butyl-1,3-dithian-2-yl)-2'-fluoro-4'-butyl-biphenyl
4-(5-butyl-1,3-dithian-2-yl)-2'-fluoro-4'-pentyl-biphenyl
4-(5-butyl-1,3-dithian-2-yl)-2'-fluoro-4'-heptyl-biphenyl
trans-1-(5-pentyl-1,3-dioxan-2-yl)-4-(4-ethyl-3-fluorophenyl)-cyclohexane
trans-1-(5-pentyl-1,3-dioxan-2-yl)-4-(4-propyl-3-fluorophenyl)-cyclohexane
trans-1-(5-pentyl-1,3-dioxan-2-yl)-4-(4-butyl-3-fluorophenyl)-cyclohexane
trans-1-(5-pentyl-1,3-dioxan-2-yl)-4-(4-pentyl-3-fluorophenyl)-cyclohexane
trans-1-(5-pentyl-1,3-dioxan-2-yl)-4-(4-heptyl-3-fluorophenyl)-cyclohexane
trans-1-(5-pentyl-1,3-dioxan-2-yl)-4-(4-ethyl-2-fluorophenyl)-cyclohexane
trans-1-(5-pentyl-1,3-dioxan-2-yl)-4-(4-propyl-2-fluorophenyl)-cyclohexane
trans-1-(5-pentyl-1,3-dioxan-2-yl)-4-(4-butyl-2-fluorophenyl)-cyclohexane
trans-1-(5-pentyl-1,3-dioxan-2-yl)-4-(4-pentyl-2-fluorophenyl)-cyclohexane
trans-1-(5-pentyl-1,3-dioxan-2-yl)-4-(4-heptyl-2-fluorophenyl)-cyclohexane
trans-1-(5-butyl-1,3-dithian-2-yl)-4-(4-ethyl-2-methylphenyl)-cyclohexane
trans-1-(5-butyl-1,3-dithian-2-yl)-4-(4-propyl-2-methylphenyl)-cyclohexane trans-1-(5-butyl-1,3-dithian-2-yl)-4-(4-butyl-2-methylphenyl)-cyclohexane
trans-1-(5-butyl-1,3-dithian-2-yl)-4-(4-pentyl-2-methylphenyl)-cyclohexane
trans-1-(5-butyl-1,3-dithian-2-yl)-4-(4-heptyl-2-methylphenyl)-cyclohexane
2-(4-ethyl-2-fluorophenyl)-5-(trans-4-pentylcyclohexyl)-1,3-dioxane
2-(4-propyl-2-fluorophenyl)-5-(trans-4-pentylcyclohexyl)-1,3-dioxane
2-(4-butyl-2-fluorophenyl)-5-(trans-4-pentylcyclohexyl)-1,3-dioxane
2-(4-pentyl-2-fluorophenyl)-5-(trans-4-pentylcyclohexyl)-1,3-dioxane
2-(4-heptyl-2-fluorophenyl)-5-(trans-4-pentylcyclohexyl)-1,3-dioxane
2-(4-ethyl-3-fluorophenyl)-5-(trans-4-pentylcyclohexyl)-1,3-dioxane
2-(4-propyl-3-fluorophenyl)-5-(trans-4-pentylcyclohexyl)-1,3-dioxane
2-(4-butyl-3-fluorophenyl)-5-(trans-4-pentylcyclohexyl)-1,3-dioxane
2-(4-penyl-3-fluorophenyl)-5-(trans-4-pentylcyclohexyl)-1,3-dioxane
2-(4-heptyl-3-fluorophenyl)-5-(trans-4-pentylcyclohexyl)-1,3-dioxane
2-(4-ethyl-2-methylphenyl)-5-(trans-4-pentylcyclohexyl)-1,3-dioxane
2-(4-propyl-2-methylphenyl)-5-(trans-4-pentylcyclohexyl)-1,3-dioxane
2-(4-butyl-2-methylphenyl)-5-(trans-4-pentylcyclohexyl)-1,3-dioxane
2-(4-pentyl-2-methylphenyl)-5-(trans-4-pentylcyclohexyl)-1,3-dioxane
2-(4-heptyl-2-methylphenyl)-5-(trans-4-pentylcyclohexyl)-1,3-dioxane
2-(4-ethyl-3-fluorophenyl)-5-(trans-4-pentylcyclohexyl)-1,3-dithiane
2-(4-propyl-3-fluorophenyl)-5-(trans-4-pentylcyclohexyl)-1,3-dithiane 2-(4-butyl-3-fluorophenyl)-5-(trans-4-pentylcyclohexyl)-1,3-dithiane
2-(4-pentyl-3-fluorophenyl)-5-(trans-4-pentylcyclohexyl)-1,3-dithiane
2-(4-heptyl-3-fluorophenyl)-5-(trans-4-pentylcyclohexyl)-1,3-dithiane
5-(5-pentyl-1,3-dioxan-2-yl)-4-fluoro-2-cyano-pyrimidine
5-(5-pentyl-1,3-dioxan-2-yl)-4-fluoro-2-ethyl-pyrimidine
5-(5-pentyl-1,3-dioxan-2-yl)-4-fluoro-2-propyl-pyrimidine
5-(5-pentyl-1,3-dioxan-2-yl)-4-fluoro-2-butyl-pyrimidine
5-(5-pentyl-1,3-dioxan-2-yl)-4-fluoro-2-pentyl-pyrimidine
5-(5-pentyl-1,3-dioxan-2-yl)-4-fluoro-2-heptyl-pyrimidine
5-(5-pentyl-1,3-dithian-2-yl)-4-fluoro-2-cyano-pyrimidine
5-(5-pentyl-1,3-dithian-2-yl)-4-fluoro-2-ethyl-pyrimidine
5-(5-pentyl-1,3-dithian-2-yl)-4-fluoro-2-propyl-pyrimidine
5-(5-pentyl-1,3-dithian-2-yl)-4-fluoro-2-butyl-pyrimidine
5-(5-pentyl-1,3-dithian-2-yl)-4-fluoro-2-pentyl-pyrimidine
5-(5-pentyl-1,3-dithian-2-yl)-4-fluoro-2-heptyl-pyrimidine
5-[4-(5-pentyl-1,3-dioxan-2-yl)-phenyl]-4-fluoro-2-cyano-pyrimidine
5-[4-(5-pentyl-1,3-dioxan-2-yl)-phenyl]-4-fluoro-2-ethyl-pyrimidine
5-[4-(5-pentyl-1,3-dioxan-2-yl)-phenyl]-4-fluoro-2-propyl-pyrimidine
5-[4-(5-pentyl-1,3-dioxan-2-yl)-phenyl]-4-fluoro-2-butyl-pyrimidine
5-[4-(5-pentyl-1,3-dioxan-2-yl)-phenyl]-4-fluoro-2-pentyl-pyrimidine
5-[4-(5-pentyl-1,3-dioxan-2-yl)-phenyl]-4-fluoro-2-heptyl-pyrimidine
5-[4-(5-propyl-1,3-dioxan-2-yl)-phenyl]-4-fluoro-2-cyano-pyrimdine
5-[4-(5-propyl-1,3-dioxan-2-yl)-phenyl]-4-fluoro-2-ethyl-pyrimidine
5-[4-(5-propyl-1,3-dioxan-2-yl)-phenyl]-4-fluoro-2-propyl-pyrimidine
5-[4-(5-propyl-1,3-dioxan-2-yl)-phenyl]-4-fluoro-2-butyl-pyrimidine 5-[4-(5-propyl-1,3-dioxan-2-yl)-phenyl]-4-fluoro-2-pentyl-pyrimidine
5-[4-(5-propyl-1,3-dioxan-2-yl)-phenyl]-4-fluoro-2-heptyl-pyrimidine
2-[4-(5-pentyl-1,3-dioxan-2-yl)-phenyl]-4-fluoro-5-cyano-pyrimidine
2-[4-(5-pentyl-1,3-dioxan-2-yl)-phenyl]-4-fluoro-5-ethyl pyrimidine
2-[4-(5-pentyl-1,3-dioxan-2-yl)-phenyl]-4-fluoro-5-propyl-pyrimidine
2-[4-(5-pentyl-1,3-dioxan-2-yl)-phenyl]-4-fluoro-5-butyl-pyrimidine
2-[4-(5-pentyl-1,3-dioxan-2-yl)-phenyl]-4-fluoro-5-pentyl-pyrimidine
2-[4-(5-pentyl-1,3-dioxan-2-yl)-phenyl]-4-fluoro-5-heptyl-pyrimidine
2-[trans-4-(5-pentyl-1,3-dioxan-2-yl)-cyclohexyl]-4-fluoro-5-cyano-pyrimidine
2-[trans-4-(5-pentyl-1,3-dioxan-2-yl)-cyclohexyl]-4-fluoro-5-ethyl-pyrimidine
2-[trans-4-(5-pentyl-1,3-dioxan-2-yl)-cyclohexyl]-4-fluoro-5-propyl-pyrimidine
2-(trans-4-(5-pentyl-1,3-dioxan-2-yl)-cyclohexyl]-4-fluoro-5-butyl-pyrimidine
2-[trans-4-(5-pentyl-1,3-dioxan-2-yl)-cyclohexyl]-4-fluoro-5-pentyl-pyrimidine
2-[trans-4-(5-pentyl-1,3-dioxan-2-yl)-cyclohexyl]-4-fluoro-5-heptyl-pyrimidine
2-[4-(5-pentyl-1,3-dioxan-2-yl)-biphenyl-4'-yl]-4-fluoro-5-cyano-pyrimidine
2-[4-(5-pentyl-1,3-dioxan-2-yl)-biphenyl-4'-yl]-4-fluoro-5-ethyl-pyrimidine
2-[4-(5-pentyl-1,3-dioxan-2-yl)-biphenyl-4'-yl]-4-fluoro-5-propyl-pyrimidine
2-[4-(5-pentyl-1,3-dioxan-2-yl)-biphenyl-4'-yl]-4-fluoro-5-butyl-pyrimidine
2-[4-(5-pentyl-1,3-dioxan-2-yl)-biphenyl-4'-yl]-4-fluoro-5-pentyl-pyrimidine
2-[4-(5-pentyl-1,3-dioxan-2-yl)-biphenyl-4'-yl]-4-fluoro-5-heptyl-pyrimidine
2-[4-(5-butyl-1,3-dithian-2-yl)-biphenyl-4'-yl]-4-fluoro-5-cyano-pyrimidine
2-[4-(5-butyl-1,3-dithian-2-yl)-biphenyl-4'-yl]-4-fluoro-5-ethyl-pyrimidine
2-[4-(5-butyl-1,3-dithian-2-yl)-biphenyl-4'-yl]-4-fluoro-5-propyl-pyrimidine
2-[4-(5-butyl-1,3-dithian-2-yl)-biphenyl-4'-yl]-4-fluoro-5-butyl-pyrimidine
2-[4-(5-butyl-1,3-dithian-2-yl)-biphenyl-4'-yl]-4-fluoro-5-pentyl-pyrimidine
2-[4-(5-butyl-1,3-dithian-2-yl)-biphenyl-4'-yl]-4-fluoro-5-heptyl-pyrimidine

EXAMPLE 3

6 g of 3-(4'-pentyl-2-fluorobiphenyl-4-yl)-propionaldehyde (obtainable by reaction of 4-(2-fluoro-4'-pentylbiphenylyl)-magnesium bromide with ethylene oxide and subsequent oxidation of the resulting alcohol with pyridinium chlorochromate) and 3.5 g of 2-heptyl-propane-1,3-diol are heated with a spatula tip of p-toluenesulfonic acid in 100 ml of toluene, using a water separator, until no further water is foamed. After cooling, the mixture is washed with bicarbonate solution and water until neutral and dried over sodium sulfate and the toluene is distilled off. After customary working-up, 1-(4'-pentyl-2-fluorobiphenyl-4-yl)-2-(5-heptyl-1,3-dioxan-2-yl)-ethane is obtained.

The following compounds are prepared analogously:
1-(4'-ethyl-2-fluorobiphenyl-4-yl)-2-(5-heptyl-1,3-dioxan-2-yl)-ethane
1-(4'-propyl-2-fluorobiphenyl-4-yl)-2-(5-heptyl-1,3-dioxan-2-yl)-ethane
1-(4'-butyl-2-fluorobiphenyl-4-yl)-2-(5-heptyl-1,3-dioxan-2-yl)-ethane
1-(4'-pentyl-2-fluorobiphenyl-4-yl)-2-(5-heptyl-1,3-dioxan-2-yl)-ethane
1-(4'-heptyl-2-fluorobiphenyl-4-yl)-2-(5-heptyl-1,3-dioxan-2-yl)-ethane
1-(4'-cyano-2-fluorobiphenyl-4-yl)-2-(5-heptyl-1,3-dioxan-2-yl)-ethane
1-(4'-ethoxy-2-fluorobiphenyl-4-yl)-2-(5-heptyl-1,3-dioxan-2-yl)-ethane
1-(4'-propoxy-2-fluorobiphenyl-4-yl)-2-(5-heptyl-1,3-dioxan-2-yl)-ethane
1-(4'-butoxy-2-fluorobiphenyl-4-yl)-2-(5-heptyl-1,3-dioxan-2-yl)-ethane
1-(4'-pentoxy-2-fluorobiphenyl-4-yl)-2-(5-heptyl-1,3-dioxan-2-yl)-ethane 1-(4'-heptoxy-2-fluorobiphenyl-4-yl)-2-(5-heptyl-1,3-dioxan-2-yl)-ethane
1-(4'-nonoxy-2-fluorobiphenyl-4-yl)-2-(5-heptyl-1,3-dioxan-2-yl)-ethane
1-(4'-ethyl-2'-fluorobiphenyl-4-yl)-2-(5-heptyl-1,3-dioxan-2-yl)-ethane
1-(4'-propyl-2'-fluorobiphenyl-4-yl)-2-(5-heptyl-1,3-dioxan-2-yl)-ethane
1-(4'-butyl-2'-fluorobiphenyl-4-yl)-2-(5-heptyl-1,3-dioxan-2-yl)-ethane
1-(4'-pentyl-2'-fluorobiphenyl-4-yl)-2-(5-heptyl-1,3-dioxan-2-yl)-ethane
1-(4'-heptyl-2'-fluorobiphenyl-4-yl)-2-(5-heptyl-1,3-dioxan-2-yl)-ethane
1-(4'-cyano-2'-fluorobiphenyl-4-yl)-2-(5-heptyl-1,3-dioxan-2-yl)-ethane
1-(4'-ethoxy-2'-fluorobiphenyl-4-yl)-2-(5-heptyl-1,3-dioxan-2-yl)-ethane
1-(4'-propoxy-2'-fluorobiphenyl-4-yl)-2-(5-heptyl-1,3-dioxan-2-yl)-ethane
1-(4'-butoxy-2'-fluorobiphenyl-4-yl)-2-(5-heptyl-1,3-dioxan-2-yl)-ethane
1-(4'-pentoxy-2'-fluorobiphenyl-4-yl)-2-(5-heptyl-1,3-dioxan-2-yl)-ethane
1-(4'-heptoxy-2'-fluorobiphenyl-4-yl)-2-(5-heptyl-1,3-dioxan-2-yl)-ethane
1-(4'-nonoxy-2'-fluorobiphenyl-4-yl)-2-(5-heptyl-1,3-dioxan-2-yl)-ethane
1-(4'-ethyl-2'-fluorobiphenyl-4-yl)-2-(5-pentyl-1,3-dioxan-2-yl)-ethane
1-(4'-propyl-2'-luorobiphenyl-4-yl)-2-(5-pentyl-1,3-dioxan-2-yl)-ethane
1-(4'-butyl-2'-fluorobiphenyl-4-yl)-2-(5-pentyl-1,3-dioxan-2-yl)-ethane
1-(4'-heptyl-2'-fluorobiphenyl-4-yl)-2-(5-pentyl-1,3-dioxan-2-yl)-ethane
1-(4'-cyano-2'-fluorobiphenyl-4-yl)-2-(5-pentyl-1,3-dioxan-2-yl)-ethane
1-(4'-ethoxy-2'-fluorobiphenyl-4-yl)-2-(5-pentyl-1,3-dioxan-2-yl)-ethane
1-(4'-propoxy-2'-fluorobiphenyl-4-yl)-2-(5-pentyl-1,3-dioxan-2-yl)-ethane
1-(4'-butoxy-2'-fluorobiphenyl-4-yl)-2-(5-pentyl-1,3-dioxan-2-yl)-ethane
1-(4'-pentoxy-2'-fluorobiphenyl-4-yl)-2-(5-pentyl-1,3-dioxan-2-yl)-ethane
1-(4'-heptoxy-2'-fluorobiphenyl-4-yl)-2-(5-pentyl-1,3-dioxan-2-yl)-ethane
1-(4'-nonoxy-2'-fluorobiphenyl-4-yl)-2-(5-pentyl-1,3-dioxan-2-yl)-ethane
1-(4'-ethyl-2'-fluorobiphenyl-4-yl)-2-(5-propyl-1,3-dioxan-2-yl)-ethane
1-(4'-propyl-2'-fluorobiphenyl-4-yl)-2-(5-propyl-1,3-dioxan-2-yl)-ethane
1-(4'-butyl-2'-fluorobiphenyl-4-yl)-2-(5-propyl-1,3-dioxan-2-yl)-ethane
1-(4'-pentyl-2'-fluorobiphenyl-4-yl)-2-(5-propyl-1,3-dioxan-2-yl)-ethane, m.p. 36°, c.p. 98°
1-(4'-heptyl-2'-fluorobiphenyl-4-yl)-2-(5-propyl-1,3-dioxan-2-yl)-ethane
1-(4'-cyano-2'-fluorobiphenyl-4-yl)-2-(5-propyl-1,3-dioxan-2-yl)-ethane
1-(4'-ethoxy-2'-fluorobiphenyl-4-yl)-2-(5-propyl-1,3-dioxan-2-yl)-ethane
1-(4'-propoxy-2'-fluorobiphenyl-4-yl)-2-(5-propyl-1,3-dioxan-2-yl)-ethane
1-(4'-butoxy-2'-fluorobiphenyl-4-yl)-2-(5-propyl-1,3-dioxan-2-yl)-ethane
1-(4'-pentoxy-2'-fluorobiphenyl-4-yl)-2-(5-propyl-1,3-dioxan-2-yl)-ethane
1-(4'-heptoxy-2'-fluorobiphenyl-4-yl)-2-(5-propyl-1,3-dioxan-2-yl)-ethane
1-(4'-nonoxy-2'-fluorobiphenyl-4-yl)-2-(5-propyl-1,3-dioxan-2-yl)-ethane
1-(4'-ethyl-2'-fluorobiphenyl-4-yl)-2-(5-butyl-1,3-dithian-2-yl)-ethane
1-(4'-propyl-2'-fluorobiphenyl-4-yl)-2-(5-butyl-1,3-dithian-2-yl)-ethane
1-(4'-butyl-2'-fluorobiphenyl-4-yl)-2-(5-butyl-1,3-dithian-2-yl)-ethane
1-(4'-pentyl-2'-fluorobiphenyl-4-yl)-2-(5-butyl-1,3-dithian-2-yl)-ethane
1-(4'-heptyl-2'-fluorobiphenyl-4-yl)-2-(5-butyl-1,3-dithian-2-yl)-ethane
1-(4'-cyano-2'-fluorobiphenyl-4-yl)-2-(5-butyl-1,3-dithian-2-yl)-ethane
1-(4'-ethoxy-2'-fluorobiphenyl-4-yl)-2-(5-butyl-1,3-dithian-2-yl)-ethane
1-(4'-propoxy-2'-fluorobiphenyl-4-yl)-2-(5-butyl-1,3-dithian-2-yl)-ethane
1-(4'-butoxy-2'-fluorobiphenyl-4-yl)-2-(5-butyl-1,3-dithian-2-yl)-ethane
1-(4'-pentoxy-2'-fluorobiphenyl-4-yl)-2-(5-butyl-1,3-dithian-2-yl)-ethane
1-(4'-heptoxy-2'-fluorobiphenyl-4-yl)-2-(5-butyl-1,3-dithian-2-yl)-ethane
1-(4'-nonoxy-2'-fluorobiphenyl-4-yl)-2-(5-butyl-1,3-dithian-2-yl)-ethane
1-(4-ethyl-2-fluorophenyl)-2-(5-pentyl-1,3-dioxan-2-yl)-ethane
1-(4-propyl-2-fluorophenyl)-2-(5-pentyl-1,3-dioxan-2-yl)-ethane
1-(4-butyl-2-fluorophenyl)-2-(5-pentyl-1,3-dioxan-2-yl)-ethane
1-(4-pentyl-2-fluorophenyl)-2-(5-pentyl-1,3-dioxan-2-yl)-ethane
1-(4-heptyl-2-fluorophenyl)-2-(5-pentyl-1,3-dioxan-2-yl)-ethane
1-(4-cyano-2-fluorophenyl)-2-(5-pentyl-1,3-dioxan-2-yl)-ethane
1-(4-ethoxy-2-fluorophenyl)-2-(5-pentyl-1,3-dioxan-2-yl)-ethane
1-(4-propoxy-2-fluorophenyl)-2-(5-pentyl-1,3-dioxan-2-yl)-ethane
1-(4-butoxy-2-fluorophenyl)-2-(5-pentyl-1,3-dioxan-2-yl)-ethane
1-(4-pentoxy-2-fluorophenyl)-2-(5-pentyl-1,3-dioxan-2-yl)-ethane
1-(4-heptoxy-2-fluorophenyl)-2-(5-pentyl-1,3-dioxan-2-yl)-ethane
1-(4-nonoxy-2-fluorophenyl)-2-(5-pentyl-1,3-dioxan-2-yl)-ethane
1-[4'-(trans-4-ethylcyclohexyl)-2'-fluorobiphenyl-4-yl]-2-(5-pentyl-1,3-dioxan-2-yl)-ethane
1-[4'-(trans-4-propylcyclohexyl)-2'-fluorobiphenyl-4-yl]-2-(5-pentyl-1,3-dioxan-2-yl)-ethane
1-[4'-(trans-4-butylcyclohexyl)-2'-fluorobiphenyl-4-yl]-2-(5-pentyl-1,3-dioxan-2-yl)-ethane
1-[4'-(trans-4-pentylcyclohexyl)-2'-fluorobiphenyl-4-yl]-2-(5-pentyl-1,3-dioxan-2-yl)-ethane
1-[4'-(trans-4-heptylcyclohexyl)-2'-fluorobiphenyl-4-yl]-2-(5-pentyl-1,3-dioxan-2-yl)-ethane
1-[p-(5-propyl-1,3-dioxan-2-yl)-phenyl]-2-(trans-4-ethylcyclohexyl)-ethane
1-[p-(5-propyl-1,3-dioxan-2-yl)-phenyl]-2-(trans-4-propylcyclohexyl)-ethane 1-[p-(5-propyl-1,3-dioxan-2-yl)-phenyl]-2-(trans-4-butylcyclohexyl)-ethane
1-[p-(5-propyl-1,3-dioxan-2-yl)-phenyl]-2-(trans-4-pentylcyclohexyl)-ethane
1-[p-(5-propyl-1,3-dioxan-2-yl)-phenyl]-2-(trans-4-heptylcyclohexyl)-ethane
1-[p-(5-butyl-1,3-dithian-2-yl)-phenyl]-2-(trans-4-ethylcyclohexyl)-ethane
1-[p-(5-butyl-1,3-dithian-2-yl)-phenyl]-2-(trans-4-propylcyclohexyl)-ethane
1-[p-(5-butyl-1,3-dithian-2-yl)-phenyl]-2-(trans-4-butylcyclohexyl)-ethane
1-[p-(5-butyl-1,3-dithian-2-yl)-phenyl]-2-(trans-4-pentylcyclohexyl)-ethane
1-[p-(5-butyl-1,3-dithian-2-yl)-phenyl]-2-(trans-4-heptylcyclohexyl)-ethane
1-[4-(trans-4-ethylcyclohexyl)-2-fluorophenyl]-2-(5-hepthyl-1,3-dioxan-2-yl)-ethane
1-[4-(trans-4-propylcyclohexyl)-2-fluorophenyl]-2-(5-heptyl-1,3-dioxan-2-yl)-ethane
1-[4-(trans-4-butylcyclohexyl)-2-fluorophenyl]-2-(5-heptyl-1,3-dioxan-2-yl)-ethane
1-[4-(trans-4-pentylcyclohexyl)-2-fluorophenyl]-2-(5-heptyl-1,3-dioxan-2-yl)-ethane
1-[4-(trans-4-heptylcyclohexyl)-2-fluorophenyl]-2-(5-heptyl-1,3-dioxan-2-yl)-ethane
1-[4-(trans-4-ethylcyclohexyl)-3-fluorophenyl]-2-(5-pentyl-1,3-dioxan-2-yl)-ethane
1-[4-(trans-4-propylcyclohexyl)-3-fluorophenyl]-2-(5-pentyl-1,3-dioxan-2-yl)-ethane
1-[4-(trans-4-butylcyclohexyl)-3-fluorophenyl]-2-(5-pentyl-1,3-dioxan-2-yl)-ethane
1-[4-(trans-4-pentylcyclohexyl)-3-fluorophenyl]-2-(5-pentyl-1,3-dioxan-2-yl)-ethane
1-[4-(trans-4-heptylcyclohexyl)-3-fluorophenyl]-2-(5-pentyl-1,3-dioxan-2-yl)-ethane
1-(4'-cyano-3'-fluorobiphenyl-4-yl)-2-(5-methyl-1,3-dioxan-2-yl)-ethane
1-(4'-cyano-3'-fluorobiphenyl-4-yl)-2-(5-ethyl-1,3-dioxan-2-yl)-ethane
1-(4'-cyano-3'-fluorobiphenyl-4-yl)-2-(5-propyl-1,3-dioxan-2-yl)-ethane
1-(4'-cyano-3'-fluorobiphenyl-4-yl)-2-(5-butyl-1,3-dioxan-2-yl)-ethane
1-(4'-cyano-3'-fluorobiphenyl-4-yl)-2-(5-pentyl-1,3-dioxan-2-yl)-ethane
1-(4'-cyano-3'-fluorobiphenyl-4-yl)-2-(5-hexyl-1,3-dioxan-2-yl)-ethane
1-(4'-cyano-3'-fluorobiphenyl-4-yl)-2-(5-heptyl-1,3-dioxan-2-yl)-ethane
1-(4'-cyano-3'-fluorobiphenyl-4-yl)-2-(5-octyl-1,3-dioxan-2-yl)-ethane

EXAMPLE 4

0.3 g of thionyl chloride are added to 0.5 g of 2-hexyl-1,3-dioxane-5-carboxylic acid (French Patent A2,521,581), 10 ml of ether and 0.2 ml of pyridine at 0°. After two hours, the pyridine hydrochloride is filtered off with suction and 2 ml of pyridine and 0.75 g of 5-hydroxy-2-propoxybenzonitrile are added to the filtrate. After 3 hours, the mixture is worked up in the customary manner. 3-Cyano-4-propoxyphenyl 2-n-hexyl-1,3-dioxane-5-carboxylate is obtained.

The following compounds are prepared analogously:
3-cyano-4-ethoxyphenyl 2-hexyl-1,3-dioxane-5-carboxylate
3-cyano-4-butoxyphenyl 2-hexyl-1,3-dioxane-5-carboxylate
3-cyano-4-pentoxyphenyl 2-hexyl-1,3-dioxane-5-carboxylate
3-cyano-4-heptoxyphenyl 2-hexyl-1,3-dioxane-5-carboxylate
3-cyano-4-cyanophenyl 2-hexyl-1,3-dioxane-5-carboxylate
2-fluoro-4-ethylphenyl 2-pentyl-1,3-dioxane-5-carboxylate
2-fluoro-4-propylphenyl 2-pentyl-1,3-dioxane-5-carboxylate
2-fluoro-4-butylphenyl 2-pentyl-1,3-dioxane-5-carboxylate
2-fluoro-4-pentylphenyl 2-pentyl-1,3-dioxane-5-carboxylate
2-fluoro-4-heptylphenyl 2-pentyl-1,3-dioxane-5-carboxylate
2-fluoro-4-cyanophenyl 2-pentyl-1,3-dioxane-5-carboxylate
2-fluoro-4-ethoxyphenyl 2-pentyl-1,3-dioxane-5-carboxylate
2-fluoro-4-propoxyphenyl 2-pentyl-1,3-dioxane-5-carboxylate
2-fluoro-4-butoxyphenyl 2-pentyl-1,3-dioxane-5-carboxylate
2-fluoro-4-pentoxyphenyl 2-pentyl-1,3-dioxane-5-carboxylate
2-fluoro-4-hexoxyphenyl 2-pentyl-1,3-dioxane-5-carboxylate
2-fluoro-4-octoxyphenyl 2-pentyl-1,3-dioxane-5-carboxylate
2-methyl-4-ethylphenyl 2-pentyl-1,3-dioxane-5-carboxylate
2-methyl-4-propylphenyl 2-pentyl-1,3-dioxane-5-carboxylate
2-methyl-4-butylphenyl 2-pentyl-1,3-dioxane-5-carboxylate
2-methyl-4-pentylphenyl 2-pentyl-1,3-dioxane-5-carboxylate
2-methyl-4-heptylphenyl 2-pentyl-1,3-dioxane-5-carboxylate
2-methyl-4-cyanophenyl 2-pentyl-1,3-dioxane-5-carboxylate
2-methyl-4-ethoxyphenyl 2-pentyl-1,3-dioxane-5-carboxylate
2-methyl-4-propoxyphenyl 2-pentyl-1,3-dioxane-5-carboxylate
2-methyl-4-butoxyphenyl 2-pentyl-1,3-dioxane-5-carboxylate
2-methyl-4-pentoxyphenyl 2-pentyl-1,3-dioxane-5-carboxylate
2-methyl-4-hexoxyphenyl 2-pentyl-1,3-dioxane-5-carboxylate
2-methyl-4-octoxyphenyl 2-pentyl-1,3-dioxane-5-carboxylate
2'-fluoro-4'-ethylbiphenyl-4-yl 2-pentyl-1,3-dioxane-5-carboxylate
2'-fluoro-4'-propylbiphenyl-4-yl 2-pentyl-1,3-dioxane-5-carboxylate
2'-fluoro-4'-butylbiphenyl-4-yl 2-pentyl-1,3-dioxane-5-carboxylate
2'-fluoro-4'-pentylbiphenyl-4-yl 2-pentyl-1,3-dioxane-5-carboxylate
2'-fluoro-4'-heptylbiphenyl-4-yl 2-pentyl-1,3-dioxane-5-carboxylate
2'-fluoro-4'-cyanobiphenyl-4-yl 2-pentyl-1,3-dioxane-5-carboxylate
2'-fluoro-4'-ethoxybiphenyl-4-yl 2-pentyl-1,3-dioxane-5-carboxylate 2'-fluoro-4'-propoxybiphenyl-4-yl 2-pentyl-1,3-dioxane-5-carboxylate
2'-fluoro-4'-butoxybiphenyl-4-yl 2-pentyl-1,3-dioxane-5-carboxylate
2'-fluoro-4'-pentoxybiphenyl-4-yl 2-pentyl-1,3-dioxane-5-carboxylate
2'-fluoro-4'-hexoxybiphenyl-4-yl 2-pentyl-1,3-dioxane-5-carboxylate
2'-fluoro-4'-octoxybiphenyl-4-yl 2-pentyl-1,3-dioxane-5-carboxylate
2-fluoro-4'-ethylbiphenyl-4-yl 2-pentyl-1,3-dioxane-5-carboxylate
2-fluoro-4'-propylbiphenyl-4-yl 2-pentyl-1,3-dioxane-5-carboxylate
2-fluoro-4'-butylbiphenyl-4-yl 2-pentyl-1,3-dioxane-5-carboxylate
2-fluoro-4'-pentylbiphenyl-4-yl 2-pentyl-1,3-dioxane-5-carboxylate
2-fluoro-4'-heptylbiphenyl-4-yl 2-pentyl-1,3-dioxane-5-carboxylate
2-fluoro-4'-cyanobiphenyl-4-yl 2-pentyl-1,3-dioxane-5-carboxylate
2-fluoro-4'-ethoxybiphenyl-4-yl 2-pentyl-1,3-dioxane-5-carboxylate
2-fluoro-4'-propoxybiphenyl-4-yl 2-pentyl-1,3-dioxane-5-carboxylate
2-fluoro-4'-butoxybiphenyl-4-yl 2-pentyl-1,3-dioxane-5-carboxylate
2-fluoro-4'-pentoxybiphenyl-4-yl 2-pentyl-1,3-dioxane-5-carboxylate
2-fluoro-4'-hexoxybiphenyl-4-yl 2-pentyl-1,3-dioxane-5-carboxylate
2-fluoro-4'-octoxybiphenyl-4-yl 2-pentyl-1,3-dioxane-5-carboxylate

EXAMPLE 5

A mixture of 3.0 g of 4-cyano-3-fluorobenzaldehyde obtainable from 2-fluoro-4-nitrotoluene by oxidation to the corresponding benzoic acid, conversion into the corresponding nitrile, reduction to 2-fluoro-4-aminobenzonitrile and conversion of the corresponding diazonium salt with formaldoxime into the aldehyde in accordance with the method of Beech (J. Chem. Soc. 1297 (1954)); the target product is also obtainable from 2-fluoro-4-aminotoluene by conversion into 3-fluoro-4-methylbenzonitrile by the Sandmeyer method, hydrolysis of the nitrile, bromination of the side chain of the ethyl 3-fluoro-4-methylbenzoate obtainable, conversion into the aldehyde by the Sommelet method, conversion of the resulting oxime into ethyl 3-fluoro-4-cyanobenzoate, reduction to 3-fluoro-4-cyanobenzyl alcohol and subsequent oxidation to the target product) and 3.5 g of 2-n-heptylpropane-1,3-diol is heated together with 1 g of strongly acid cation exchanger in 100 ml of toluene for 8 hours using a water separator. The catalyst is then filtered off and the toluene is removed. After customary working-up, 2-(4-cyano-3-fluorophenyl)-5-n-heptyl-1,3-dioxane is obtained.

The following compounds are prepared analogously:
2-(4-cyano-3-fluorophenyl)-5-methyl-1,3-dioxane
2-(4-cyano-3-fluorophenyl)-5-ethyl-1,3-dioxane
2-(4-cyano-3-fluorophenyl)-5-propyl-1,3-dioxane
2-(4-cyano-3-fluorophenyl)-5-butyl-1,3-dioxane
2-(4-cyano-3-fluorophenyl)-5-pentyl-1,3-dioxane
2-(4-cyano-3-fluorophenyl)-5-hexyl-1,3-dioxane
2-(4-cyano-3-fluorophenyl)-5-octyl-1,3-dioxane

EXAMPLE 6

A mixture of 2.8 g of p-(5-n-pentyl-1,3-dioxan-2-yl)-benzoic acid (German Offenlegungsschrift 3,146,249), 1.6 g of 4-cyano-3-fluorophenol, 2.1 g of dicyclohexylcarbodiimide, 0.1 g of 4-dimethylaminopyridine and 30 ml of N,N-dimethylformamide is stirred at 0° C. for 8 hours. After warming to room temperature, 50 ml of methylene chloride are added and the urea obtained is filtered off. The filtrate is washed successively with hydrochloric acid, sodium bicarbonate and water and worked up in the customary manner. 4-Cyano-3-fluorophenyl p-(5-n-pentyl-1,3-dioxan-2-yl)-benzoate is obtained.

The following compounds are prepared analogously:
4-cyano-3-fluorophenyl p-(5-methyl-1,3-dioxan-2-yl)-benzoate
4-cyano-3-fluorophenyl p-(5-ethyl-1,3-dioxan-2-yl)-benzoate
4-cyano-3-fluorophenyl p-(5-propyl-1,3-dioxan-2-yl)-benzoate
4-cyano-3-fluorophenyl p-(5-butyl-1,3-dioxan-2-yl)-benzoate
4-cyano-3-fluorophenyl p-(5-hexyl-1,3-dioxan-2-yl)-benzoate
4-cyano-3-fluorophenyl p-(5-heptyl-1,3-dioxan-2-yl)-benzoate
4-cyano-3-fluorophenyl p-(5-octyl-1,3-dioxan-2-yl)-benzoate

EXAMPLE 7

A mixture of 3.0 g of 4-cyano-3-fluorobenzaldehyde and 4.0 g of 2-(trans-4-n-propylcyclohexyl)-propane-1,3-diol is reacted analogously to Example 5. 2-(4-Cyano-3-fluorophenyl)-5-(trans-4-n-propylcyclohexyl)-1,3-dioxane is obtained. The following compounds are prepared analogously:
2-(4-cyano-3-fluorophenyl)-5-(trans-4-methylcyclohexyl)-1,3-dioxane
2-(4-cyano-3-fluorophenyl)-5-(trans-4-ethylcyclohexyl)-1,3-dioxane
2-(4-cyano-3-fluorophenyl)-5-(trans-4-butylcyclohexyl)-1,3-dioxane
2-(4-cyano-3-fluorophenyl)-5-(trans-4-pentylcyclohexyl)-1,3-dioxane
2-(4-cyano-3-fluorophenyl)-5-(trans-4-hexylcyclohexyl)-1,3-dioxane
2-(4-cyano-3-fluorophenyl)-5-(trans-4-heptylcyclohexyl)-1,3-dioxane
2-(4-cyano-3-fluorophenyl)-5-(trans-4-octylcyclohexyl)-1,3-dioxane

EXAMPLE 8

4-Cyano-3-fluorophenyl 2-n-hexyl-1,3-dioxane-5-carboxylate is obtained from 2-n-hexyl-1,3-dioxane-5-carboxylic acid and 4-cyano-3-fluorophenol analogously to Example 6.

The following compounds are prepared analogously:
4-cyano-3-fluorophenyl 2-methyl-1,3-dioxane-5-carboxylate
4-cyano-3-fluorophenyl 2-ethyl-1,3-dioxane-5-carboxylate
4-cyano-3-fluorophenyl 2-propyl-1,3-dioxane-5-carboxylate
4-cyano-3-fluorophenyl 2-butyl-1,3-dioxane-5-carboxylate
4-cyano-3-fluorophenyl 2-pentyl-1,3-dioxane-5-carboxylate 4-cyano-3-fluorophenyl 2-heptyl-1,3-dioxane-5-carboxylate 4-cyano-3-fluorophenyl 2-octyl-1,3-dioxane-5-carboxylate

EXAMPLE 9

2.96 gms. of 3-fluoro-4-(5-pentyl-1,3-dioxan-2-yl)-benzoic acid (prepared from 2-fluoro-4-bromotoluene by reaction with magnesium according to Grignard and reaction with carbon dioxide giving 3-fluoro-4-methyl-benzoic acid, esterification thereof with ethanol/sulfuric acid giving ethyl 3-fluoro-4-methyl-benzoate, bromination by bromine or N-bromo-succinimide giving ethyl 3-fluoro-4-bromomethylbenzoate, oxidation by dilute nitric acid giving 3-fluoro-terephthalic aldehydic acid and ketalization thereof with 2-pentyl-propane-1,3-diol) and 2.0 gms. of $SOCl_2$ are boiled for 1 hour, then evaporated and the crude acid chloride thus obtained is dissolved in 20 ml of toluene and then 1.5 ml of pyridine and 1.10 gms. of 4-cyano-phenol are added and then boiled for two hours. After separation the organic phase is washed with water, dried over sodium sulfate and evaporated leaving behind 4-cyanophenyl 3-fluoro-4-(5-pentyl-1,3-dioxan-2-yl)-benzoate.

Analogously are obtained:

4-cyanphenyl 3-fluoro-4-(5-ethyl-1,3-dioxan-2-yl)-benzoate 4-cyanphenyl 3-fluoro-4-(5-propyl-1,3-dioxan-2-yl)-benzoate 4-cyanphenyl 3-fluoro-4-(5-butyl-1,3-dioxan-2-yl)-benzoate 4-cyanphenyl 3-fluoro-4-(5-hexyl-1,3-dioxan-2-yl)-benzoate 4-cyanphenyl 3-fluoro-4-(5-heptyl-1,3-dioxan-2-yl)-benzoate 4-cyanphenyl 3-fluoro-4-(5-octyl-1,3-dioxan-2-yl)-benzoate 4-cyanphenyl 3-fluoro-4-(5-nonyl-1,3-dioxan-2-yl)-benzoate 4-ethylphenyl 3-fluoro-4-(5-ethyl-1,3-dioxan-2-yl)-benzoate 4-ethylphenyl 3-fluoro-4-(5-propyl-1,3-dioxan-2-yl)-benzoate 4-ethylphenyl 3-fluoro-4-(5-butyl-1,3-dioxan-2-yl)-benzoate 4-ethylphenyl 3-fluoro-4-(5-pentyl-1,3-dioxan-2-yl)-benzoate 4-ethylphenyl 3-fluoro-4-(5-hexyl-1,3-dioxan-2-yl)-benzoate 4-ethylphenyl 3-fluoro-4-(5-heptyl-1,3-dioxan-2-yl)-benzoate 4-ethylphenyl 3-fluoro-4-(5-octyl-1,3-dioxan-2-yl)-benzoate 4-ethylphenyl 3-fluoro-4-(5-nonyl-1,3-dioxan-2-yl)-benzoate 4-propylphenyl 3-fluoro-4-(5-ethyl-1,3-dioxan-2-yl)-benzoate 4-propylphenyl 3-fluoro-4-(5-propyl-1,3-dioxan-2-yl)-benzoate 4-propylphenyl 3-fluoro-4-(5-butyl-1,3-dioxan-2-yl)-benzoate 4-propylphenyl 3-fluoro-4-(5-pentyl-1,3-dioxan-2-yl)-benzoate 4-propylphenyl 3-fluoro-4-(5-hexyl-1,3-dioxan-2-yl)-benzoate 4-propylphenyl 3-fluoro-4-(5-heptyl-1,3-dioxan-2-yl)-benzoate 4-propylphenyl 3-fluoro-4-(5-octyl-1,3-dioxan-2-yl)-benzoate 4-propylphenyl 3-fluoro-4-(5-nonyl-1,3-dioxan-2-yl)-benzoate 4-butylphenyl 3-fluoro-4-(5-ethyl-1,3-dioxan-2-yl)-benzoate 4-butylphenyl 3-fluoro-4-(5-propyl-1,3-dioxan-2-yl)-benzoate 4-butylphenyl 3-fluoro-4-(5-butyl-1,3-dioxan-2-yl)-benzoate 4-butylphenyl 3-fluoro-4-(5-pentyl-1,3-dioxan-2-yl)-benzoate 4-butylphenyl 3-fluoro-4-(5-hexyl-1,3-dioxan-2-yl)-benzoate 4-butylphenyl 3-fluoro-4-(5-heptyl-1,3-dioxan-2-yl)-benzoate 4-butylphenyl 3-fluoro-4-(5-octyl-1,3-dioxan-2-yl)-benzoate 4-butylphenyl 3-fluoro-4-(5-nonyl-1,3-dioxan-2-yl)-benzoate 4-pentylphenyl 3-fluoro-4-(5-ethyl-1,3-dioxan-2-yl)-benzoate 4-pentylphenyl 3-fluoro-4-(5-propyl-1,3-dioxan-2-yl)-benzoate 4-pentylphenyl 3-fluoro-4-(5-butyl-1,3-dioxan-2-yl)-benzoate 4-pentylphenyl 3-fluoro-4-(5-pentyl-1,3-dioxan-2-yl)-benzoate 4-pentylphenyl 3-fluoro-4-(5-hexyl-1,3-dioxan-2-yl)-benzoate 4-pentylphenyl 3-fluoro-4-(5-heptyl-1,3-dioxan-2-yl)-benzoate 4-pentylphenyl 3-fluoro-4-(5-octyl-1,3-dioxan-2-yl)-benzoate 4-pentylphenyl 3-fluoro-4-(5-nonyl-1,3-dioxan-2-yl)-benzoate 4-hexylphenyl 3-fluoro-4-(5-ethyl-1,3-dioxan-2-yl)-benzoate 4-hexylphenyl 3-fluoro-4-(5-propyl-1,3-dioxan-2-yl)-benzoate 4-hexylphenyl 3-fluoro-4-(5-butyl-1,3-dioxan-2-yl)-benzoate 4-hexylphenyl 3-fluoro-4-(5-pentyl-1,3-dioxan-2-yl)-benzoate 4-hexylphenyl 3-fluoro-4-(5-hexyl-1,3-dioxan-2-yl)-benzoate 4-hexylphenyl 3-fluoro-4-(5-heptyl-1,3-dioxan-2-yl)-benzoate 4-hexylphenyl 3-fluoro-4-(5-octyl-1,3-dioxan-2-yl)-benzoate 4-hexylphenyl 3-fluoro-4-(5-nonyl-1,3-dioxan-2-yl)-benzoate 4-heptylphenyl 3-fluoro-4-(5-ethyl-1,3-dioxan-2-yl)-benzoate 4-heptylphenyl 3-fluoro-4-(5-propyl-1,3-dioxan-2-yl)-benzoate 4-heptylphenyl 3-fluoro-4-(5-butyl-1,3-dioxan-2-yl)-benzoate 4-heptylphenyl 3-fluoro-4-(5-pentyl-1,3-dioxan-2-yl)-benzoate 4-heptylphenyl 3-fluoro-4-(5-hexyl-1,3-dioxan-2-yl)-benzoate 4-heptylphenyl 3-fluoro-4-(5-heptyl-1,3-dioxan-2-yl)-benzoate 4-heptylphenyl 3-fluoro-4-(5-octyl-1,3-dioxan-2-yl)-benzoate 4-heptylphenyl 3-fluoro-4-(5-nonyl-1,3-dioxan-2-yl)-benzoate 4-octylphenyl 3-fluoro-4-(5-ethyl-1,3-dioxan-2-yl)-benzoate
4-octylphenyl 3-fluoro-4-(5-propyl-1,3-dioxan-2-yl)-benzoate
4-octylphenyl 3-fluoro-4-(5-butyl-1,3-dioxan-2-yl)-benzoate
4-octylphenyl 3-fluoro-4-(5-pentyl-1,3-dioxan-2-yl)-benzoate
4-octylphenyl 3-fluoro-4-(5-hexyl-1,3-dioxan-2-yl)-benzoate
4-octylphenyl 3-fluoro-4-(5-heptyl-1,3-dioxan-2-yl)-benzoate
4-octylphenyl 3-fluoro-4-(5-octyl-1,3-dioxan-2-yl)-benzoate
4-octylphenyl 3-fluoro-4-(5-nonyl-1,3-dioxan-2-yl)-benzoate
4-nonylphenyl 3-fluoro-4-(5-ethyl-1,3-dioxan-2-yl)-benzoate
4-nonylphenyl 3-fluoro-4-(5-propyl-1,3-dioxan-2-yl)-benzoate
4-nonylphenyl 3-fluoro-4-(5-butyl-1,3-dioxan-2-yl)-benzoate
4-nonylphenyl 3-fluoro-4-(5-pentyl-1,3-dioxan-2-yl)-benzoate
4-nonylphenyl 3-fluoro-4-(5-hexyl-1,3-dioxan-2-yl)-benzoate
4-nonylphenyl 3-fluoro-4-(5-heptyl-1,3-dioxan-2-yl)-benzoate
4-nonylphenyl 3-fluoro-4-(5-octyl-1,3-dioxan-2-yl)-benzoate
4-nonylphenyl 3-fluoro-4-(5-nonyl-1,3-dioxan-2-yl)-benzoate
4-ethoxyphenyl 3-fluoro-4-(5-ethyl-1,3-dioxan-2-yl)-benzoate
4-ethoxyphenyl 3-fluoro-4-(5-propyl-1,3-dioxan-2-yl)-benzoate
4-ethoxyphenyl 3-fluoro-4-(5-butyl-1,3-dioxan-2-yl)-benzoate
4-ethoxyphenyl 3-fluoro-4-(5-pentyl-1,3-dioxan-2-yl)-benzoate
4-ethoxyphenyl 3-fluoro-4-(5-hexyl-1,3-dioxan-2-yl)-benzoate
4-ethoxyphenyl 3-fluoro-4-(5-heptyl-1,3-dioxan-2-yl)-benzoate
4-ethoxyphenyl 3-fluoro-4-(5-octyl-1,3-dioxan-2-yl)-benzoate
4-ethoxyphenyl 3-fluoro-4-(5-nonyl-1,3-dioxan-2-yl)-benzoate
4-propoxyphenyl 3-fluoro-4-(5-ethyl-1,3-dioxan-2-yl)-benzoate
4-propoxyphenyl 3-fluoro-4-(5-propyl-1,3-dioxan-2-yl)-benzoate
4-propoxyphenyl 3-fluoro-4-(5-butyl-1,3-dioxan-2-yl)-benzoate
4-propoxyphenyl 3-fluoro-4-(5-pentyl-1,3-dioxan-2-yl)-benzoate
4-propoxyphenyl 3-fluoro-4-(5-hexyl-1,3-dioxan-2-yl)-benzoate
4-propoxyphenyl 3-fluoro-4-(5-heptyl-1,3-dioxan-2-yl)-benzoate
4-propoxyphenyl 3-fluoro-4-(5-octyl-1,3-dioxan-2-yl)-benzoate
4-propoxyphenyl 3-fluoro-4-(5-nonyl-1,3-dioxan-2-yl)-benzoate
4-butoxyphenyl 3-fluoro-4-(5-ethyl-1,3-dioxan-2-yl)-benzoate
4-butoxyphenyl 3-fluoro-4-(5-propyl-1,3-dioxan-2-yl)-benzoate
4-butoxyphenyl 3-fluoro-4-(5-butyl-1,3-dioxan-2-yl)-benzoate
4-butoxyphenyl 3-fluoro-4-(5-pentyl-1,3-dioxan-2-yl)-benzoate
4-butoxyphenyl 3-fluoro-4-(5-hexyl-1,3-dioxan-2-yl)-benzoate
4-butoxyphenyl 3-fluoro-4-(5-heptyl-1,3-dioxan-2-yl)-benzoate
4-butoxyphenyl 3-fluoro-4-(5-octyl-1,3-dioxan-2-yl)-benzoate
4-butoxyphenyl 3-fluoro-4-(5-nonyl-1,3-dioxan-2-yl)-benzoate
4-pentoxyphenyl 3-fluoro-4-(5-ethyl-1,3-dioxan-2-yl)-benzoate
4-pentoxyphenyl 3-fluoro-4-(5-propyl-1,3-dioxan-2-yl)-benzoate
4-pentoxyphenyl 3-fluoro-4-(5-butyl-1,3-dioxan-2-yl)-benzoate
4-pentoxyphenyl 3-fluoro-4-(5-pentyl-1,3-dioxan-2-yl)-benzoate
4-pentoxyphenyl 3-fluoro-4-(5-hexyl-1,3-dioxan-2-yl)-benzoate
4-pentoxyphenyl 3-fluoro-4-(5-heptyl-1,3-dioxan-2-yl)-benzoate
4-pentoxyphenyl 3-fluoro-4-(5-octyl-1,3-dioxan-2-yl)-benzoate
4-pentoxyphenyl 3-fluoro-4-(5-nonyl-1,3-dioxan-2-yl)-benzoate
4-hexoxyphenyl 3-fluoro-4-(5-ethyl-1,3-dioxan-2-yl)-benzoate
4-hexoxyphenyl 3-fluoro-4-(5-propyl-1,3-dioxan-2-yl)-benzoate
4-hexoxyphenyl 3-fluoro-4-(5-butyl-1,3-dioxan-2-yl)-benzoate
4-hexoxyphenyl 3-fluoro-4-(5-pentyl-1,3-dioxan-2-yl)-benzoate
4-hexoxyphenyl 3-fluoro-4-(5-hexyl-1,3-dioxan-2-yl)-benzoate
4-hexoxyphenyl 3-fluoro-4-(5-heptyl-1,3-dioxan-2-yl)-benzoate
4-hexoxyphenyl 3-fluoro-4-(5-octyl-1,3-dioxan-2-yl)-benzoate
4-hexoxyphenyl 3-fluoro-4-(5-nonyl-1,3-dioxan-2-yl)-benzoate
4-heptoxyphenyl 3-fluoro-4-(5-ethyl-1,3-dioxan-2-yl)-benzoate
4-heptoxyphenyl 3-fluoro-4-(5-propyl-1,3-dioxan-2-yl)-benzoate
4-heptoxyphenyl 3-fluoro-4-(5-butyl-1,3-dioxan-2-yl)-benzoate
4-heptoxyphenyl 3-fluoro-4-(5-pentyl-1,3-dioxan-2-yl)-benzoate
4-heptoxyphenyl 3-fluoro-4-(5-hexyl-1,3-dioxan-2-yl)-benzoate
4-heptoxyphenyl 3-fluoro-4-(5-heptyl-1,3-dioxan-2-yl)-benzoate
4-heptoxyphenyl 3-fluoro-4-(5-octyl-1,3-dioxan-2-yl)-benzoate
4-heptoxyphenyl 3-fluoro-4-(5-nonyl-1,3-dioxan-2-yl)-benzoate
4-octoxyphenyl 3-fluoro-4-(5-ethyl-1,3-dioxan-2-yl)-benzoate
4-octoxyphenyl 3-fluoro-4-(5-propyl-1,3-dioxan-2-yl)-benzoate
4-octoxyphenyl 3-fluoro-4-(5-butyl-1,3-dioxan-2-yl)-benzoate
4-octoxyphenyl 3-fluoro-4-(5-pentyl-1,3-dioxan-2-yl)-benzoate 4-octoxyphenyl 3-fluoro-4-(5-hexyl-1,3-dioxan-2-yl)-benzoate
4-octoxyphenyl 3-fluoro-4-(5-heptyl-1,3-dioxan-2-yl)-benzoate
4-octoxyphenyl 3-fluoro-4-(5-octyl-1,3-dioxan-2-yl)-benzoate
4-octoxyphenyl 3-fluoro-4-(5-nonyl-1,3-dioxan-2-yl)-benzoate
4-nonoxyphenyl 3-fluoro-4-(5-ethyl-1,3-dioxan-2-yl)-benzoate
4-nonoxyphenyl 3-fluoro-4-(5-propyl-1,3-dioxan-2-yl)-benzoate
4-nonoxyphenyl 3-fluoro-4-(5-butyl-1,3-dioxan-2-yl)-benzoate
4-nonoxyphenyl 3-fluoro-4-(5-pentyl-1,3-dioxan-2-yl)-benzoate
4-nonoxyphenyl 3-fluoro-4-(5-hexyl-1,3-dioxan-2-yl)-benzoate
4-nonoxyphenyl 3-fluoro-4-(5-heptyl-1,3-dioxan-2-yl)-benzoate
4-nonoxyphenyl 3-fluoro-4-(5-octyl-1,3-dioxan-2-yl)-benzoate
4-nonoxyphenyl 3-fluoro-4-(5-nonyl-1,3-dioxan-2-yl)-benzoate
ethyl 3-fluoro-4-(5-ethyl-1,3-dioxan-2-yl)-benzoate
ethyl 3-fluoro-4-(5-propyl-1,3-dioxan-2-yl)-benzoate
ethyl 3-fluoro-4-(5-butyl-1,3-dioxan-2-yl)-benzoate
ethyl 3-fluoro-4-(5-pentyl-1,3-dioxan-2-yl)-benzoate
ethyl 3-fluoro-4-(5-hexyl-1,3-dioxan-2-yl)-benzoate
ethyl 3-fluoro-4-(5-heptyl-1,3-dioxan-2-yl)-benzoate
ethyl 3-fluoro-4-(5-octyl-1,3-dioxan-2-yl)-benozoate
ethyl 3-fluoro-4-(5-nonyl-1,3-dioxan-2-yl)-benzoate
propyl 3-fluoro-4-(5-ethyl-1,3-dioxan-2-yl)-benzoate
propyl 3-fluoro-4-(5-propyl-1,3-dioxan-2-yl)-benzoate
propyl 3-fluoro-4-(5-butyl-1,3-dioxan-2-yl)-benzoate
propyl 3-fluoro-4-(5-pentyl-1,3-dioxan-2-yl)-benzoate
propyl 3-fluoro-4-(5-hexyl-1,3-dioxan-2-yl)-benzoate
propyl 3-fluoro-4-(5-heptyl-1,3-dioxan-2-yl)-benzoate
propyl 3-fluoro-4-(5-octyl-1,3-dioxan-2-yl)-benzoate
propyl 3-fluoro-4-(5-nonyl-1,3-dioxan-2-yl)-benzoate
butyl 3-fluoro-4-(5-ethyl-1,3-dioxan-2-yl)-benzoate
butyl 3-fluoro-4-(5-propyl-1,3-dioxan-2-yl)-benzoate
butyl 3-fluoro-4-(5-butyl-1,3-dioxan-2-yl)-benzoate
butyl 3-fluoro-4-(5-pentyl-1,3-dioxan-2-yl)-benzoate
butyl 3-fluoro-4-(5-hexyl-1,3-dioxan-2-yl)-benzoate
butyl 3-fluoro-4-(5-heptyl-1,3-dioxan-2-yl)-benzoate
butyl 3-fluoro-4-(5-octyl-1,3-dioxan-2-yl)-benzoate
butyl 3-fluoro-4-(5-nonyl-1,3-dioxan-2-yl)-benzoate
pentyl 3-fluoro-4-(5-ethyl-1,3-dioxan-2-yl)-benzoate
pentyl 3-fluoro-4-(5-propyl-1,3-dioxan-2-yl)-benzoate
pentyl 3-fluoro-4-(5-butyl-1,3-dioxan-2-yl)-benzoate
pentyl 3-fluoro-4-(5-pentyl-1,3-dioxan-2-yl)-benzoate
pentyl 3-fluoro-4-(5-hexyl-1,3-dioxan-2-yl)-benzoate
pentyl 3-fluoro-4-(5-heptyl-1,3-dioxan-2-yl)-benzoate
pentyl 3-fluoro-4-(5-octyl-1,3-dioxan-2-yl)-benzoate
pentyl 3-fluoro-4-(5-nonyl-1,3-dioxan-2-yl)-benzoate
hexyl 3-fluoro-4-(5-ethyl-1,3-dioxan-2-yl)-benzoate
hexyl 3-fluoro-4-(5-propyl-1,3-dioxan-2-yl)-benzoate
hexyl 3-fluoro-4-(5-butyl-1,3-dioxan-2-yl)-benzoate
hexyl 3-fluoro-4-(5-pentyl-1,3-dioxan-2-yl)-benzoate
hexyl 3-fluoro-4-(5-hexyl-1,3-dioxan-2-yl)-benzoate
hexyl 3-fluoro-4-(5-heptyl-1,3-dioxan-2-yl)-benzoate
hexyl 3-fluoro-4-(5-octyl-1,3-dioxan-2-yl)-benzoate
hexyl 3-fluoro-4-(5-nonyl-1,3-dioxan-2-yl)-benzoate
heptyl 3-fluoro-4-(5-ethyl-1,3-dioxan-2-yl)-benzoate
heptyl 3-fluoro-4-(5-propyl-1,3-dioxan-2-yl)-benzoate
heptyl 3-fluoro-4-(5-butyl-1,3-dioxan-2-yl)-benzoate
heptyl 3-fluoro-4-(5-pentyl-1,3-dioxan-2-yl)-benzoate
heptyl 3-fluoro-4-(5-hexyl-1,3-dioxan-2-yl)-benzoate
heptyl 3-fluoro-4-(5-heptyl-1,3-dioxan-2-yl)-benzoate
heptyl 3-fluoro-4-(5-octyl-1,3-dioxan-2-yl)-benzoate
heptyl 3-fluoro-4-(5-nonyl-1,3-dioxan-2-yl)-benzoate
octyl 3-fluoro-4-(5-ethyl-1,3-dioxan-2-yl)-benzoate
octyl 3-fluoro-4-(5-propyl-1,3-dioxan-2-yl)-benzoate
octyl 3-fluoro-4-(5-butyl-1,3-dioxan-2-yl)-benzoate
octyl 3-fluoro-4-(5-pentyl-1,3-dioxan-2-yl)-benzoate
octyl 3-fluoro-4-(5-hexyl-1,3-dioxan-2-yl)-benzoate
octyl 3-fluoro-4-(5-heptyl-1,3-dioxan-2-yl)-benzoate
octyl 3-fluoro-4-(5-octyl-1,3-dioxan-2-yl)-benzoate
octyl 3-fluoro-4-(5-nonyl-1,3-dioxan-2-yl)-benzoate
nonyl 3-fluoro-4-(5-ethyl-1,3-dioxan-2-yl)-benzoate
nonyl 3-fluoro-4-(5-propyl-1,3-dioxan-2-yl)-benzoate
nonyl 3-fluoro-4-(5-butyl-1,3-dioxan-2-yl)-benzoate
nonyl 3-fluoro-4-(5-pentyl-1,3-dioxan-2-yl)-benzoate
nonyl 3-fluoro-4-(5-hexyl-1,3-dioxan-2-yl)-benzoate
nonyl 3-fluoro-4-(5-heptyl-1,3-dioxan-2-yl)-benzoate
nonyl 3-fluoro-4-(5-octyl-1,3-dioxan-2-yl)-benzoate
nonyl 3-fluoro-4-(5-nonyl-1,3-dioxan-2-yl)-benzoate

EXAMPLE 10

As described in Example 9 4.44 gms. of 3-fluoro-4-(5-pentyl-1,3-dioxan-2-yl)-benzoic acid are converted by SOCl$_2$ into the acid chloride. After removing excess SOCl$_2$ the residue obtained is added to aqueous ammonia and stirred for 4 hours at 20° C. The precipitated acid amide is filtrated by suction and dried. For conversion into the nitrile it is dissolved in 50 ml of pyridine and 10 ml of POCl$_3$, then stirred at 20° C. for 20 hours and evaporated. Thus 3-fluoro-4-(5-pentyl-1,3-dioxan-2-yl)-benzonitrile is obtained.

Analogously are obtained:
3-fluoro-4-(5-ethyl-1,3-dioxan-2-yl)-benzonitrile
3-fluoro-4-(5-propyl-1,3-dioxan-2-yl)-benzonitrile
3-fluoro-4-(5-butyl-1,3-dioxan-2-yl)-benzonitrile
3-fluoro-4-(5-pentyl-1,3-dioxan-2-yl)-benzonitrile
3-fluoro-4-(5-hexyl-1,3-dioxan-2-yl)-benzonitrile
3-fluoro-4-(5-heptyl-1,3-dioxan-2-yl)-benzonitrile
3-fluoro-4-(5-octyl-1,3-dioxan-2-yl)-benzonitrile
3-fluoro-4-(5-nonyl-1,3-dioxan-2-yl)-benzonitrile The examples which follow relate to liquid crystal phases according to the invention.

EXAMPLE A

A liquid crystal phase of
15% of p-trans-4-propylcyclohexyl-benzonitrile,
11% of p-trans-4-pentylcyclohexyl-benzonitrile,
15% of trans-1-p-methoxyphenyl-4-propylcyclohexane,
5% of trans-1-p-ethoxyphenyl-4-propylcyclohexane,
6% of 4-cyano-4'-(trans-4-pentylcyclohexyl)-biphenyl,
12% of 4-ethyl-4'-(trans-4-propylcyclohexyl)-biphenyl,
8% of 4-ethyl-4'-(trans-4-pentylcyclohexyl)-biphenyl,
5% of 4,4'-bis-(trans-4-propylcyclohexyl)-biphenyl,
6% of 4-(trans-4-pentylcyclohexyl)-4'-(trans-4-propylcyclohexyl)-biphenyl,
6% of 4-(trans-4-pentylcyclohexyl)-2-fluoro-4'-(5-propyl-1,3-dioxan-2-yl)-biphenyl,
4% of p-methoxyphenyl trans-4-propylcyclohexanecarboxylate
3% of p-ethoxyphenyl trans-4-propylcyclohexanecarboxylate and
4% of p-methoxyphenyl trans-4-butylcyclohexanecarboxylate
has a clear point of 106° and an optical anisotropy Δn of +0.13.

EXAMPLE B

A liquid crystal phase is prepared from:
10% of 2-p-cyanophenyl-5-butyl-1,3-dioxane,
11% of p-trans-4-pentylcyclohexyl-benzonitrile,
16% of p-trans-4-propylcyclohexyl-benzonitrile,
8% of 4-ethyl-4'-cyanobiphenyl
7% of 4-propyl-4'-cyanobiphenyl
13% of 4-(trans-4-pentylcyclohexyl)-2-fluoro-4'-(5-propyl-1,3-dioxan-2-yl)-biphenyl,
8% of 4-(trans-4-propylcyclohexyl)-2-fluoro-4'-(5-propyl-1,3-dioxan-2-yl)-biphenyl,
9% of 4-(trans-4-pentylcyclohexyl)-2-methyl-4'-(5-propyl-1,3-dioxan-2-yl)-biphenyl,
8% of 4-cyano-4'-(trans-4-propylcyclohexyl)-biphenyl and
10% of 4,4'-bis-(trans-4-propylcyclohexyl)-biphenyl.

EXAMPLE C

A liquid crystal phase is prepared from:
16% of p-trans-4-propylcyclohexyl-benzonitrile,
12% of p-trans-4-pentylcyclohexyl-benzonitrile,
15% of trans-1-p-methoxyphenyl-4-propylcyclohexane,
5% of trans-1-p-ethoxyphenyl-4-propylcyclohexane,
7% of 4-cyano-4'-(trans-4-pentylcyclohexyl)-biphenyl,
13% of 4-ethyl-4'-(trans-4-propylcyclohexyl)-biphenyl,
8% of 4-ethyl-4'-(trans-4-pentylcyclohexyl)-biphenyl,
5% of 4,4'-bis-(trans-4-propylcyclohexyl)-biphenyl,
7% of 4-(trans-4-pentylcyclohexyl)-4'-(trans-4-propylcyclohexyl)-biphenyl,
0.5% of 4-(trans-4-pentylcyclohexyl)-2-fluoro-4'-(5-propyl-1,3-dioxan-2-yl)-biphenyl,
4.5% of p-methoxyphenyl trans-4-propylcyclohexanecarboxylate,
3% of p-ethoxyphenyl trans-4-propylcyclohexanecarboxylate, and
4% of p-methoxyphenyl trans-4-butylcyclohexanecarboxylate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystalline phase comprising at least two components, the improvement wherein at least one component is a compound of the formula $$R^1—A^1—Z^1—A^2—R^2$$

wherein
$R^1$ and $R^2$ each independently is H, an alkyl, alkoxy, alkanoyl, alkanoyloxy or alkoxycarbonyl group in each case of 1-10 C atoms, F, Cl, Br, CN or $R^3—A^3—Z^2$—,
$A^1$ is —A—, —$A^4$—A— or —A—$A^4$—,
A is 1,3-dioxane-2,5-diyl,
$A^2$, $A^3$ each independently is 1,4-cyclohexylene, 1,4-phenylene
and $A^4$ or 1,4-phenylene, which is substituted by F,
$Z^1$ and $Z^2$ each independently is —CO—O—, O—CO—, —CH$_2$CH$_2$—, —OCH$_2$—, —CH$_2$O or a single bond and $R^3$ is H, an alkyl, alkoxy, alkanoyl, alkanoyloxy or alkoxycarbonyl group in each case of 1-10 C atoms, F, Cl, Br or CN,
with the proviso that
(a) at least one group of $A^2$, $A^3$ and $A^4$ contains a single lateral substituent,
(b) 1,3-dioxane-2,5-diyl is not substituted by alkoxy, alkanoyl, alkanoyloxy, alkoxycarbonyl, F, Cl, Br, CN or $R^3—A^3—Z^2$ in the 2-position and
(c) $Z^1$ is not —CH$_2$CH$_2$— when $A^1$ is —A—.

2. A phase of claim 1 wherein at least one component is a compound of the formula $$R^1—A—Z^1—A^2—R^2.$$

3. A phase of claim 1 wherein at least one component is a compound of the formula $$R^1—A^4—A—Z^1—A^2—R^2$$

$$R^1—A—A^4—Z^1—A^2—R^2$$

$$R^1—A—Z^1—Z^2—A^3—R^3$$

$$R^3—A^3—Z^2—A—Z^1—A^2—R^2$$

$$R^1—A—Z^1—A^2—A^3—R^2$$

$$R^1—A—A^2—Z^2—A^3—R^3$$

$$R^3—A^3—Z^2—A—A^2—R^2$$

$$R^3—A^3—A—Z^1—A^2—R^2.$$

4. A phase of claim 1 wherein at least one component is a compound of the formula $$R^3—A^3—Z^2—A—Z^1—A^2—Z^2—A^3—R^3$$

$$R^3—A^3—A—Z^1—A^2—A^3—R^3$$

$$R^3—A^3—Z^2—A—A^2—A^3—R^3$$

$$R^3—A^3—A—A^2—Z^2—A^3—R^3$$

$$R^1—A^4—A—Z^1—A^2—Z^2—A^3—R^3$$

$$R^3—A^3—Z^2—A^4—A—Z^1—A^2—R^2$$

$$R^1—A—A^4—Z^1—A^2—Z^2—A^3—R^3$$

$$R^3—A^3—Z^2—A—A^4—Z^1—A^2—R^2$$

$$R^1—A^4—A—A^2—Z^2—A^3—R^3$$

$$R^1—A—A^4—A^2—Z^2—A^3—R^3$$

$$R^1—A^4—A—Z^1—A^2—A^3—R^3$$

$$R^1—A—A^4—Z^1—A^2—A^3—R^3$$

$$R^3—A^3—A^4—A—Z^1—A^2—R^2$$

$$R^3—A^3—A—A^4—Z^1—A^2—R^2$$

$$R^3—A^3—Z^2—A^4—A—A^2—R^2$$

$$R^3—A^3—Z^2—A—A^4—A^2—R^2.$$

5. A phase of claim 1 wherein at least one component is a compound of the formula $$R^3—A^3—Z^2—A^4—A—Z^1—A^2—Z^2—A^3—R^3$$

$$R^3—A^3—Z^2—A—A^4—Z^1—A^2—Z^2—A^3—R^3$$

$$R^3—A^3—A^4—A—Z^1—A^2—A^3—R^3$$

$$R^3—A^3—A—A^4—Z^1—A^2—A^3—R^3.$$

6. A phase of claim 1 wherein at least one component is a compound wherein $R^1$ and $R^2$ each is alkyl or alkoxy.

7. A phase of claim 1 wherein at least one component is a compound wherein $R^1$ and $R^2$ each is CN, F, Cl, alkyl or alkoxy.

8. A phase of claim 1 wherein at least one component is a compound wherein $A^2$, $A^3$ and $A^4$ each is 1,4-cyclohexylene or 1,4-phenylene.

9. A phase of claim 1 wherein at least one component is a compound wherein $Z^1$ and $Z^2$ each is —CO—O—, —O—CO— or a single bond.

10. A phase of claim 1 wherein at least one component is a compound of the formula $R^1$—Dio—COO—Phe—$R^2$ $R^1$—Dio—OCO—Phe—$R^2$ $R^1$—Dio—Phe—OCO—Phe—$R^2$ $R^1$—Dio—Phe—CH$_2$CH$_2$—Phe—$R^2$ $R^1$—Dio—Phe—CH$_2$CH$_2$—Cy—$R^2$ $R^1$—Dio—Phe—CH$_2$CH$_2$—Phe—Cy—$R^3$ $R^1$—Dio—Phe—$R^2$ $R^1$—Dio—Phe—Phe—$R^2$ $R^1$—Dio—Phe—Phe—Cy—$R^3$ $R^1$—Dio—Cy—Phe—$R^2$ $R^1$—Cy—Dio—Phe—$R^2$ $R^1$—Dio—CH$_2$CH$_2$—Phe—Phe—$R^2$ $R^1$—Dio—CH$_2$CH$_2$—Phe—Phe—Cy—$R^2$ $R^1$—Dio—CH$_2$CH$_2$—Phe—Cy—$R^2$ wherein Cy is 1,4-cyclohexylene, Dio is 1,3-dioxane-2,5-diyl, Phe is 1,4-phenylene or is 1,4-phenylene with a single lateral substituent and each compound contains one lateral substituent.

11. A phase of claim 1 wherein at least one component is a compound of the formula $R^1$—Dio—$A^4$—CO—O—Q—CN wherein Dio is 1,3-dioxane-2,5-diyl, Q is 3-fluoro-1,4-phenylene and $A^4$ is 1,4-phenylene or 1,4-cyclohexylene.

12. In a liquid crystal display element, comprising a liquid crystal phase, the improvement wherein the phase is one of claim 1.

13. In an electrooptical display element comprising a liquid crystal dielectric, the improvement wherein the dielectric is a phase of claim 1.

* * * * *